(12) United States Patent
Biju

(10) Patent No.: US 7,897,606 B2
(45) Date of Patent: Mar. 1, 2011

(54) 5,6-DI-SUBSTITUTED OXADIAZOLOPYRAZINES AND THIADIAZOLOPYRAZINES AS CXC-CHEMOKINE RECEPTOR LIGANDS

(75) Inventor: Purakkattle J. Biju, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 1224 days.

(21) Appl. No.: 11/475,789

(22) Filed: Jun. 27, 2006

(65) Prior Publication Data

US 2007/0015731 A1    Jan. 18, 2007

Related U.S. Application Data

(60) Provisional application No. 60/695,162, filed on Jun. 29, 2005.

(51) Int. Cl.
   *A61K 31/4965* (2006.01)
(52) U.S. Cl. .................. 514/255.05; 544/350; 549/505
(58) Field of Classification Search ............ 514/255.05; 544/350; 549/505
   See application file for complete search history.

(56) References Cited

U.S. PATENT DOCUMENTS

| | | | |
|---|---|---|---|
| 4,170,588 | A | 10/1979 | Hegenberg et al. |
| 4,639,523 | A | 1/1987 | Nohara et al. |
| 5,206,252 | A | 4/1993 | Butera et al. |
| 5,354,763 | A | 10/1994 | Butera et al. |
| 5,397,790 | A | 3/1995 | Butera et al. |
| 5,401,753 | A | 3/1995 | Butera et al. |
| 5,403,853 | A | 4/1995 | Butera et al. |
| 5,466,712 | A | 11/1995 | Butera et al. |
| 5,506,252 | A | 4/1996 | Butera et al. |
| 5,532,245 | A | 7/1996 | Butera et al. |
| 5,840,764 | A | 11/1998 | Quagliato et al. |
| 6,300,325 | B1 | 10/2001 | Widdowson et al. |
| 6,376,555 | B1 | 4/2002 | Butera et al. |
| 6,420,396 | B1 | 7/2002 | Albers et al. |
| 2001/0018447 | A1 | 8/2001 | Widdowson et al. |
| 2003/0204085 | A1 | 10/2003 | Taveras et al. |
| 2004/0034229 | A1 | 2/2004 | Taveras et al. |
| 2004/0053953 | A1 | 3/2004 | Taveras et al. |
| 2004/0186142 | A1 | 9/2004 | Taveras et al. |
| 2006/0025453 | A1 | 2/2006 | Taveras et al. |
| 2006/0223864 | A1 | 10/2006 | Biju et al. |
| 2007/0004682 | A1 | 1/2007 | Biju |
| 2007/0264230 | A1 | 11/2007 | Taveras et al. |
| 2009/0131445 | A1* | 5/2009 | Baures et al. ............... 514/249 |

FOREIGN PATENT DOCUMENTS

| | | |
|---|---|---|
| DE | 33 09 655 A1 | 9/1984 |
| EP | 0 040 696 A2 | 12/1981 |
| EP | 0 067 436 | 12/1982 |
| EP | 0 099 121 A2 | 1/1984 |
| EP | 0 275 997 A | 7/1988 |
| EP | 0 376 079 A | 7/1990 |
| EP | 0 796 243 B1 | 9/1997 |
| EP | 1 529 531 A1 | 5/2005 |
| GB | 1186096 | 4/1970 |
| GB | 2124622 A | 2/1984 |
| GB | 2132190 A | 7/1984 |
| WO | WO 94/29277 | 12/1994 |
| WO | WO 95/14005 | 5/1995 |
| WO | WO 96/14300 | 5/1996 |
| WO | WO 96/15103 | 5/1996 |
| WO | WO 98/33763 | 8/1998 |
| WO | WO 00/20378 | 4/2000 |
| WO | WO 00/21927 A | 4/2000 |
| WO | WO 00/35855 | 6/2000 |
| WO | WO 00/35864 | 6/2000 |
| WO | WO 00/73260 A1 | 12/2000 |
| WO | WO 01/28987 | 4/2001 |
| WO | WO 01/29000 A2 | 4/2001 |
| WO | WO 01/64208 A1 | 9/2001 |
| WO | WO 01/64691 A1 | 9/2001 |
| WO | WO 01/68569 A2 | 9/2001 |
| WO | WO 01/79209 A2 | 10/2001 |
| WO | WO 01/92202 A1 | 12/2001 |
| WO | WO 02/044378 * | 6/2002 |
| WO | WO 02/057230 | 7/2002 |
| WO | WO 02/067919 | 9/2002 |
| WO | WO 02/076926 A | 10/2002 |
| WO | WO 02/083624 A1 | 10/2002 |
| WO | WO 03/031440 A1 | 4/2003 |
| WO | WO 03/057676 A1 | 7/2003 |

(Continued)

OTHER PUBLICATIONS

Starchenkov, B., et al., Chemistry of Furazono[3,4-b]Pyrazines 3. Method for the Synthesis of 5,6-Disubstitued Furazano[3,4-b]Pyrazines, Chemistry of Heterocyclic Compounds, vol. 33, No. 10, 1997, 1219-1233.

(Continued)

*Primary Examiner*—James O Wilson
*Assistant Examiner*—Douglas M Willis
(74) *Attorney, Agent, or Firm*—Eric A. Meade; Henry C. Jeanette

(57) ABSTRACT

Disclosed are compounds of the formula

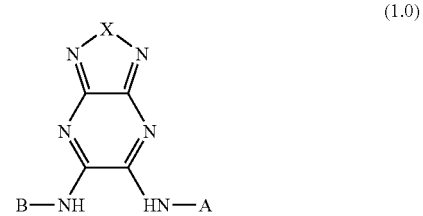

(1.0)

and the pharmaceutically acceptable salts thereof. The compounds are useful for the treatment of chemokine-mediated diseases such as COPD.

12 Claims, No Drawings

FOREIGN PATENT DOCUMENTS

| WO | WO 03/080053 A1 | 10/2003 |
|---|---|---|
| WO | WO 2004/011418 A1 | 2/2004 |
| WO | WO 2005/051974 A2 | 6/2005 |
| WO | WO 2006/044402 A1 | 4/2006 |
| WO | WO 2007/002764 A2 | 1/2007 |

OTHER PUBLICATIONS

Fernandez, E., et al., Solid-phase versus solution synthesis of asymmetrically disubstituted furazano[3,4-b]pyrazines, Tetrahedron Letters 43 (2002) 4741-4745.

PCT International Search Report dated Aug. 11, 2006, for corresponding PCT Application No. PCT/US2006/024908.

Chemical Abstract 66:18527 for Maahs, Guenther, et al., "Syntheses and derivatives of squaric acid," *Angewandte Chemie* 78(20):927-31 (1966).

Chemical Abstract 87:134383 for Augustin, Manfred, et al., "Disubstitution in 2,3-dichloromaleimides" *Zeitschrift Fuer Chemie* 17(6):215-216 (1977).

Chemical Abstract No. 87:151727 for Ehrhardt, Heinz, et at., "Amides and thioamides of squaric acid: syntheses and reactions," *Chemische Berichte* 110(7):2506-23 (1977).

Chemical Abstract 104:129517 for Gruenefeld, Johann, et al., "Reactions of squaric acid with carbodiimides," *Archiv der Pharmazie* 318(12):1062-70 (1985).

Chemical Abstract No. 122:160745 for Tillack, Annegret, et al., "Assymmetric catalysis. IV. Hydrosilylation of acetophenone with pyrroline-2,5-dione modified [Rh(COD)Cl]2 catalyst," *Journal of Organometallic Chemistry* 482:85-91 (1994).

Chemical Abstract No. 125:300482 for Chen, Yizhao, et al., "Reaction of dibutyl oxosquarate with aromatic primary amines," *Sichuan Daxue Xuebao, Ziran Kexueban* 33(2): 182-186 (1996).

Chemical Abstract No. 130:222994 for Chen, Yi-Zhao, et al., "Synthesis of asymmetric aryl-substituted amides of squaric acid and asymmetric isosquarylium amides," *Hechen Huaxue* 6(4):383-392 (1998).

Butera, John A., et al., "Design and SAR of Novel Potassium Channel Openers Targeted for Urge Urinary Incontinence. 1. *N*-Cyanoguanidine Bioisosteres Possessing in Vivo Bladder Selectivity," *J. Med. Chem.* 43:1187-1202 (2000).

Davis, Peter D., et al., "Inhibitors of protein kinase C 1. 2,3-Bisarylmaleimides," *J. Med. Chem.* 35:177-184 (1992).

Hanaineh-Abdelnour, Leila, et al., "Some synthetic applications of 2,3-Dichloro-*N*-phenylmaleimide: A Novel Synthesis of 2-Phenylpyrrolo[3,4-b]quinoxaline-1,3-diones. I," *Tetrahedron* 55:11859-11870 (1999).

Hoffman, Jacob M., et al., "Conformational Requirements of Histamine $H_2$-Receptor Inhibitors: Structure-Activity Study of Phenylene Analogues Related to Cimetidine and Tiotidine," *Journal of Medicinal Chemistry* 26(2):140-44 (1983).

Karady, Sandor, et al., "1,2,5-Thiadiazole-1-Oxides.I.Synthesis and Reactions of Alkoxy and Alkythio Analogs," *Heterocycles* 16(9):1561-4 (1981).

Martinez, Ana, et al., "Synthesis of Nonsymmetrically 3,4-Disubstituted 1,2,5-Thiadiazole Dioxides," *Journal of Heterocyclic Chemistry* 35(2):297-300 (1998).

Neuse, Eberhard W., et al., "Poly(squaryl amides)" *Polymer* 15:339-45 (1974).

Patent Abstracts of Japan, vol. 018, No. 361 (c-1222), Jul. 7, 1994 and JP 06 092915A, Apr. 5, 1994 abstract.

Schostarez, Heinrich J., et al., "Cyanoguanidine Bioisosteres in Potassium Channel Openers: evaluation of 3,4-Disubstituted-1,2,5-Thiadiazole-1-Oxides," *Bioorganic & Medicinal Chemistry Letters* 6(18):2187-92 (1996).

Wen, Richard Y., et al., "The Chemistry of 1,2,5-Thiadiazoles. II. 3,4-Disubstituted Derivatives of 1,2,5-Thiadiazole 1,1-Dioxide," *J. Org. Chem.* 40(19):2743-8 (1975).

Zhou, Hai-Bing, et al., "Design, synthesis and structure of new chiral squaric acid monoaminoalcohols and diaminoalcohols and their use as catalysts in asymmetric reduction of ketones and diketones," *Tetrahedron* 57:9325-9333 (2001).

\* cited by examiner

5,6-DI-SUBSTITUTED OXADIAZOLOPYRAZINES AND THIADIAZOLOPYRAZINES AS CXC-CHEMOKINE RECEPTOR LIGANDS

REFERENCE TO RELATED APPLICATION

This application claims the benefit of U.S. Provisional Application No. 60/695,162 filed Jun. 29, 2005.

FIELD OF THE INVENTION

The present invention relates to novel substituted oxadiazolopyrazine and thiadiazolopyrazine compounds, pharmaceutical compositions containing the compounds, and the use of the compounds and formulations in treating CXC chemokine-mediated diseases.

BACKGROUND OF THE INVENTION

Chemokines are chemotactic cytokines that are released by a wide variety of cells to attract macrophages, T-cells, eosinophils, basophils, neutrophils and endothelial cells to sites of inflammation and tumor growth. There are two main classes of chemokines, the CXC-chemokines and the CC-chemokines. The class depends on whether the first two cysteines are separated by a single amino acid (CXC-chemokines) or are adjacent (CC-chemokines). The CXC-chemokines include interleukin-8 (IL-8), neutrophil-activating protein-1 (NAP-1), neutrophil-activating protein-2 (NAP-2), GROα, GROβ, GROγ, ENA-78, GCP-2, IP-10, MIG and PF4. CC chemokines include RANTES, MIP-1α, MIP-2β, monocyte chemotactic protein-1 (MCP-1), MCP-2, MCP-3 and eotaxin. Individual members of the chemokine families are known to be bound by at least one chemokine receptor, with CXC-chemokines generally bound by members of the CXCR class of receptors, and CC-chemokines by members of the CCR class of receptors. For example, IL-8 is bound by the CXCR-1 and CXCR-2 receptors.

Since CXC-chemokines promote the accumulation and activation of neutrophils, these chemokines have been implicated in a wide range of acute and chronic inflammatory disorders including psoriasis and rheumatoid arthritis. Baggiolini et al., FEBS Left. 307, 97 (1992); Miller et al., Crit. Rev. Immunol. 12, 17 (1992); Oppenheim et al., Annu. Fev. Immunol. 9, 617 (1991); Seitz et al., J. Clin. Invest. 87, 463 (1991); Miller et al., Am. Rev. Respir. Dis. 146, 427 (1992); Donnely et al., Lancet 341, 643 (1993).

ELRCXC chemokines including IL-8, GROα, GROβ, GROγ, NAP-2, and ENA-78 (Strieter et al. 1995 JBC 270 p. 27348-57) have also been implicated in the induction of tumor angiogenesis (new blood vessel growth). All of these chemokines are believed to exert their actions by binding to the 7 transmembrane G-protein coupled receptor CXCR2 (also known as IL-8RB), while IL-8 also binds CXCR1 (also known as IL-8RA). Thus, their angiogenic activity is due to their binding to and activation of CXCR2, and possible CXCR1 for IL-8, expressed on the surface of vascular endothelial cells (ECs) in surrounding vessels.

Many different types of tumors have been shown to produce ELRCXC chemokines and their production has been correlated with a more aggressive phenotype (Inoue et al. 2000 Clin Cancer Res 6 p. 2104-2119) and poor prognosis (Yoneda et. al. 1998 J Nat Cancer Inst 90 p. 447-454). Chemokines are potent chemotactic factors and the ELRCXC chemokines have been shown to induce EC chemotaxis. Thus, these chemokines probably induce chemotaxis of endothelial cells toward their site of production in the tumor. This may be a critical step in the induction of angiogenesis by the tumor. Inhibitors of CXCR2 or dual inhibitors of CXCR2 and CXCR1 will inhibit the angiogenic activity of the ELRCXC chemokines and therefore block the growth of the tumor. This anti-tumor activity has been demonstrated for antibodies to IL-8 (Arenberg et al. 1996 J Clin Invest 97 p. 2792-2802), ENA-78 (Arenberg et al. 1998 J Clin Invest 102 p. 465-72), and GROα (Haghnegahdar et al. J. Leukoc Biology 2000 67 p. 53-62).

Many tumor cells have also been shown to express CXCR2 and thus tumor cells may also stimulate their own growth when they secrete ELRCXC chemokines. Thus, along with decreasing angiogenesis, inhibitors of CXCR2 may directly inhibit the growth of tumor cells.

Hence, the CXC-chemokine receptors represent promising targets for the development of novel anti-inflammatory and anti-tumor agents.

There remains a need for compounds that are capable of modulating activity at CXC-chemokine receptors. For example, conditions associated with an increase in IL-8 production (which is responsible for chemotaxis of neutrophil and T-cell subsets into the inflammatory site and growth of tumors) would benefit by compounds that are inhibitors of IL-8 receptor binding.

SUMMARY OF THE INVENTION

This invention provides a method of treating a chemokine mediated disease in a patient in need of such treatment comprising administering to said patient an effective amount of a compound of formula 1.0.

This invention also provides a method of treating cancer in a patient in need of such treatment comprising administering to said patient an effective amount of a compound of formula 1.0.

This invention also provides a method of treating cancer in a patient in need of such treatment comprising administering to said patient an effective amount of a compound of formula 1.0 concurrently or sequentially with: (a) a microtubule affecting agent, or (b) an antineoplastic agent, or (c) an anti-angiogenesis agent, or (d) a VEGF receptor kinase inhibitor, or (e) antibodies against the VEGF receptor, or (f) interferon, and/or g) radiation.

This invention also provides a method of inhibiting angiogenesis, in a patient in need of such treatment, comprising administering to said patient an effective amount of at least one compound of formula 1.0.

This invention also provides a method of treating angiogenic ocular disease (e.g., ocular inflammation, retinopathy of prematurity, diabetic retinopathy, macular degeneration with the wet type preferred and corneal neovascularization) in a patient in need of such treatment, comprising administering to said patient an effective amount of at least one compound of formula 1.0.

This invention also provides a method of treating a disease selected from the group consisting of: gingivitis, respiratory viruses, herpes viruses, hepatitis viruses, HIV, kaposi's sarcoma associated virus and atherosclerosis, in a patient in need of such treatment, comprising administering to said patient an effective amount of at least one compound of formula 1.0.

This invention also provides a method of treating pain, in a patient in need of such treatment, comprising administering to said patient an effective amount of at least one compound of formula 1.0.

This invention also provides a method of treating acute inflammatory pain, in a patient in need of such treatment, comprising administering to said patient an effective amount of at least one compound of formula 1.0.

This invention also provides a method of treating chronic inflammatory pain, in a patient in need of such treatment, comprising administering to said patient an effective amount of at least one compound of formula 1.0.

This invention also provides a method of treating acute neuropathic pain, in a patient in need of such treatment, comprising administering to said patient an effective amount of at least one compound of formula 1.0.

This invention also provides a method of treating chronic neuropathic pain, in a patient in need of such treatment, comprising administering to said patient an effective amount of at least one compound of formula 1.0.

This invention also provides a method of treating COPD, in a patient in need of such treatment, comprising administering to said patient and effective amount of at least one compound of formula 1.0.

This invention also provides a method of treating acute inflammation, in a patient in need of such treatment, comprising administering to said patient and effective amount of at least one compound of formula 1.0.

This invention also provides a method of treating chronic inflammation, in a patient in need of such treatment, comprising administering to said patient and effective amount of at least one compound of formula 1.0.

This invention also provides a method of treating rheumatoid arthritis, in a patient in need of such treatment, comprising administering to said patient and effective amount of at least one compound of formula 1.0.

This invention also provides novel compounds of formula 1.0.

This invention also provides a pharmaceutical composition comprising at least one (e.g., 1-3, usually 1) compound of formula 1.0 and a pharmaceutically acceptable carrier.

DETAILED DESCRIPTION OF THE INVENTION

When any variable occurs more than one time in any moiety, its definition on each occurrence is independent of its definition at every other occurrence. Also, combinations of substituents and/or variables are permissible only if such combinations result in stable compounds.

Unless indicated otherwise, the following definitions apply throughout the present specification and claims. These definitions apply regardless of whether a term is used by itself or in combination with other terms. For example, the definition of "alkyl" also applies to the "alkyl" portion of "alkoxy".

"Anti-cancer agent", "chemotherapeutic agent", and "antineoplastic agent" have the same meaning, and these terms represent the drugs (medicaments) used to treat cancer.

"Antineoplastic agent" represents a chemotherapeutic agent effective against cancer.

"At least one" means one or more than one, e.g., 1, 2 or 3, or 1 or 2, or 1.

"Compound", with reference to the antineoplastic agents, includes the agents that are antibodies.

"Concurrently" represents (1) simultaneously in time (e.g., at the same time); or (2) at different times during the course of a common treatment schedule;

"Consecutively" (or "sequentially") means one following the other;

"Effective amount" or "therapeutically effective amount" is meant to describe an amount of compound or a composition of the present invention effective in inhibiting or treating the disease or condition (e.g., the amount effective in treating or inhibiting cancer). For example, in the treatment of cancer, the amount of the compound or composition that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor.

"Mammal" includes a human being, and preferably means a human being.

"One or more" means at least one, e.g., 1, 2 or 3, 1 or 2, or 1.

"Patient" includes both human and other mammals, preferably human.

"Sequentially" means (1) administration of one component of the method (e.g., (a) compound of the invention, or (b) chemotherapeutic agent and/or radiation therapy) followed by administration of the other component or components. After administration of one component, the next component can be administered substantially immediately after the first component, or the next component can be administered after an effective time period after the first component; the effective time period is the amount of time given for realization of maximum benefit from the administration of the first component.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as defined below (and as defined below, the alkyl, alkenyl, alkynyl, cycloalkyl, cycloalkenyl and cycloalkynyl moieties can be substituted). The bond to the parent moiety is through the carbonyl. Preferred acyls contain a lower alkyl; Non-limiting examples of suitable acyl groups include formyl, acetyl, propanoyl, 2-methylpropanoyl, butanoyl and cyclohexanoyl.

"Alkenyl" means an aliphatic hydrocarbon group (chain) comprising at least one carbon to carbon double bond, wherein the chain can be straight or branched, and wherein said group comprises about 2 to about 15 carbon atoms. Preferred alkenyl groups comprise about 2 to about 12 carbon atoms in the chain; and more preferably about 2 to about 6 carbon atoms in the chain. Branched means that one or more lower alkyl groups, such as methyl, ethyl or propyl, are attached to a linear alkenyl chain. "Lower alkenyl" means an alkenyl group comprising about 2 to about 6 carbon atoms in the chain, and the chain can be straight or branched. The term "substituted alkenyl" means that the alkenyl group is substituted by one or more independently selected substituents, and each substituent is independently selected from the group consisting of: halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkoxy" means an alkyl-O— group (i.e., the bond to the parent moiety is through the ether oxygen) in which the alkyl group is unsubstituted or substituted as described below. Non-limiting examples of suitable alkoxy groups include methoxy, ethoxy, n-propoxy, isopropoxy, n-butoxy and heptoxy.

"Alkoxycarbonyl" means an alkyl-O—CO— group (i.e., the bond to the parent moiety is through the carbonyl) wherein the alkyl group is unsubstituted or substituted as previously defined. Non-limiting examples of suitable alkoxycarbonyl groups include methoxycarbonyl and ethoxycarbonyl.

"Alkyl" (including the alkyl portions of other moieties, such as trifluoroalkyl and alkyloxy) means an aliphatic hydrocarbon group (chain) that can be straight or branched wherein said group comprises about 1 to about 20 carbon atoms in the chain. Preferred alkyl groups comprise about 1 to about 12 carbon atoms in the chain. More preferred alkyl groups comprise about 1 to about 6 carbon atoms in the chain. Branched means that one or more lower alkyl groups, such as methyl, ethyl or propyl, are attached to a linear alkyl chain. "Lower alkyl" means a group comprising about 1 to about 6 carbon atoms in the chain, and said chain can be straight or branched. The term "substituted alkyl" means that the alkyl group is substituted by one or more independently selected substituents, and wherein each substituent is independently selected from the group consisting of: halo, aryl, cycloalkyl, cyano, hydroxy, alkoxy, alkylthio, amino, —NH(alkyl), —NH(cycloalkyl), —N(alkyl)$_2$, carboxy, —C(O)O-alkyl and —S(alkyl). Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkylaryl" means an alkyl-aryl-group (i.e., the bond to the parent moiety is through the aryl group) wherein the alkyl group is unsubstituted or substituted as defined above, and the aryl group is unsubstituted or substituted as defined below. Preferred alkylaryls comprise a lower alkyl group. Non-limiting examples of suitable alkylaryl groups include o-tolyl, p-tolyl and xylyl;

"Alkylheteroaryl" means an alkyl-heteroaryl-group (i.e., the bond to the parent moiety is through the heteroaryl group) wherein the alkyl is unsubstituted or substituted as defined above and the heteroaryl group is unsubstituted or substituted as defined below.

"Alkylsulfinyl" means an alkyl-S(O)— group (i.e., the bond to the parent moiety is through the sulfinyl) wherein the alkyl group is unsubstituted or substituted as previously defined. Preferred groups are those in which the alkyl group is lower alkyl.

"Alkylsulfonyl" means an alkyl-S(O$_2$)— group (i.e., the bond to the parent moiety is through the sulfonyl) wherein the alkyl group is unsubstituted or substituted as previously defined. Preferred groups are those in which the alkyl group is lower alkyl.

"Alkylthio" means an alkyl-S— group (i.e., the bond to the parent moiety is through the sulfur) wherein the alkyl group is unsubstituted or substituted as previously described. Non-limiting examples of suitable alkylthio groups include methylthio, ethylthio, i-propylthio and heptylthio.

"Alkynyl" means an aliphatic hydrocarbon group (chain) comprising at least one carbon to carbon triple bond, wherein the chain can be straight or branched, and wherein the group comprises about 2 to about 15 carbon atoms in the. Preferred alkynyl groups comprise about 2 to about 12 carbon atoms in the chain, and more preferably about 2 to about 4 carbon atoms in the chain. Branched means that one or more lower alkyl groups, such as methyl, ethyl or propyl, are attached to a linear alkynyl chain. "Lower alkynyl" means an alkynyl group comprising about 2 to about 6 carbon atoms in the chain, and the chain can be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group is substituted by one or more independently selected, and each substituent is independently selected from the group consisting of alkyl; aryl and cycloalkyl.

"Amino" means an —NH$_2$ group.

"Aralkenyl" means an aryl-alkenyl-group (i.e., the bond to the parent moiety is through the alkenyl group) wherein the aryl group is unsubstituted or substituted as defined previously, and the alkenyl group is unsubstituted or substituted as defined previously. Preferred aralkenyls contain a lower alkenyl group. Non-limiting examples of suitable aralkenyl groups include 2-phenethenyl and 2-naphthylethenyl.

"Aralkoxycarbonyl" means an aralkyl-O—C(O)— group (i.e., the bond to the parent moiety is through the carbonyl) wherein the aralkyl group is unsubstituted or substituted as previously defined. A non-limiting example of a suitable aralkoxycarbonyl group is benzyloxycarbonyl.

"Aralkyloxy" means an aralkyl-O— group (i.e., the bond to the parent moiety is through the ether oxygen) wherein the aralkyl group is unsubstituted or substituted as previously described. Non-limiting examples of suitable aralkyloxy groups include benzyloxy and 1- or 2-naphthalenemethoxy.

"Aralkyl" or "arylalkyl" means an aryl-alkyl-group (i.e., the bond to the parent moiety is through the alkyl group) wherein the aryl is unsubstituted or substituted as defined below and the alkyl is unsubstituted or substituted as defined above. Preferred aralkyls comprise a lower alkyl group. Non-limiting examples of suitable aralkyl groups include benzyl, 2-phenethyl and naphthalenylmethyl.

"Aralkylthio" means an aralkyl-S— group (i.e., the bond to the parent moiety is through the sulfur) wherein the aralkyl group is unsubstituted or substituted as previously described. A non-limiting example of a suitable aralkylthio group is benzylthio.

"Aroyl" means an aryl-C(O)— group (i.e., the bond to the parent moiety is through the carbonyl) wherein the aryl group is unsubstituted or substituted as defined below. Non-limiting examples of suitable groups include benzoyl and 1- and 2-naphthoyl.

"Aryl" (sometimes abbreviated "ar") means an aromatic monocyclic or multicyclic ring system comprising about 6 to about 14 carbon atoms, preferably about 6 to about 10 carbon atoms. The aryl group can be optionally substituted with one or more independently selected "ring system substituents" (defined below). Non-limiting examples of suitable aryl groups include phenyl and naphthyl.

"Aryloxy" means an aryl-O— group (i.e., the bond to the parent moiety is through the ether oxygen) wherein the aryl group is unsubstituted or substituted as defined above. Non-limiting examples of suitable aryloxy groups include phenoxy and naphthoxy.

"Aryloxycarbonyl" means an aryl-O—C(O)— group (i.e., the bond to the parent moiety is through the carbonyl) wherein the aryl group is unsubstituted or substituted as previously defined. Non-limiting examples of suitable aryloxycarbonyl groups include phenoxycarbonyl and naphthoxycarbonyl.

"Arylsulfinyl" means an aryl-S(O)— group (i.e., the bond to the parent moiety is through the sulfinyl) wherein aryl is unsubstituted or substituted as previously defined.

"Arylsulfonyl" means an aryl-S(O$_2$)— group (i.e., the bond to the parent moiety is through the sulfonyl) wherein aryl is unsubstituted or substituted as previously defined.

"Arylthio" means an aryl-S— group (i.e., the bond to the parent moiety is through the sulfur) wherein the aryl group is unsubstituted or substituted as previously described. Non-limiting examples of suitable arylthio groups include phenylthio and naphthylthio.

"Cycloalkenyl" means a non-aromatic mono or multicyclic ring system comprising about 3 to about 10 carbon atoms, preferably about 5 to about 10 carbon atoms that contains at least one carbon-carbon double bond. Preferred cycloalkenyl rings contain about 5 to about 7 ring atoms. The cycloalkenyl can be optionally substituted with one or more independently selected "ring system substituents" (defined below). Non-limiting examples of suitable monocyclic cycloalkenyls include cyclopentenyl, cyclohexenyl, cycloheptenyl, and the like. A non-limiting example of a suitable multicyclic cycloalkenyl is norbornylenyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more independently selected "ring system substituents" (defined below). Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Halo" means fluoro, chloro, bromo, or iodo groups. Preferred halos are fluoro, chloro or bromo.

"Halogen" means fluorine, chlorine, bromine, or iodine. Preferred halogens are fluorine, chlorine and bromine.

"Haloalkyl" means an alkyl, as defined above, wherein one or more hydrogen atoms on the alkyl is replaced by a halo group, as defined above.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls comprise about 5 to about 6 ring atoms. The "heteroaryl" can be optionally substituted by one or more independently selected "ring system substituents" (defined below). The prefix aza, oxa or thia before the heteroaryl root name means that at least a nitrogen, oxygen or sulfur atom, respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heteroaralkyl" means a heteroaryl-alkyl-group (i.e., the bond to the parent moiety is through the alkyl group) in which the heteroaryl is unsubstituted or substituted as defined above, and the alkyl group is unsubstituted or substituted as defined above. Preferred heteroaralkyls comprise an alkyl group that is a lower alkyl group. Non-limiting examples of suitable aralkyl groups include pyridylmethyl, 2-(furan-3-yl) ethyl and quinolin-3-ylmethyl.

"Heteroaralkylthio" means a heteroaralkyl-S— group wherein the heteroaralkyl group is unsubstituted or substituted as defined above.

"Heteroarylsulfinyl" means a heteroaryl-SO— group wherein the heteroaryl group is unsubstituted or substituted as defined above.

"Heteroarylsulfonyl" means a heteroaryl-$SO_2$— group wherein the heteroaryl group is unsubstituted or substituted as defined above.

"Heteroarylthio" means a heteroaryl-S— group wherein the heteroaryl group is unsubstituted or substituted as defined above.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon (for example one or more heteroatoms independently selected from the group consisting of nitrogen, oxygen and sulfur atom), and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom, respectively, is present as a ring atom. The heterocyclenyl can be optionally substituted by one or more independently selected "Ring system substituents" (defined below). The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. A non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more independently selected "ring system substituents" (defined below). The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Hydroxyalkyl" means a HO-alkyl-group wherein the alkyl group is substituted or unsubstituted as defined above. Preferred hydroxyalkyls comprise a lower alkyl; Non-limiting examples of suitable hydroxyalkyl groups include hydroxymethyl and 2-hydroxyethyl.

"Ring system substituent" means a substituent attached to an aromatic or non-aromatic ring system that, for example, replaces an available hydrogen on the ring system. Ring system substituents are each independently selected from the group consisting of: alkyl, alkenyl, alkynyl, aryl, heteroaryl, aralkyl, alkylaryl, aralkenyl, heteroaralkyl, alkylheteroaryl, heteroaralkenyl, heteroarylalkyni, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, —C(=N—CN)—$NH_2$, —C(=NH)—$NH_2$, —C(=NH)—NH(alkyl), $Y_1Y_2N$—, $Y_1Y_2$N-alkyl-, $Y_1Y_2$NC(O)—$Y_1Y_2NSO_2$—, and —$SO_2NY_1Y_2$, wherein $Y_1$ and $Y_2$ are each independently selected from the group consisting of: hydrogen, alkyl, aryl, cycloalkyl, and aralkyl. "Ring system substituent" also means a single moiety which simultaneously replaces two available hydrogens on two adjacent carbon atoms (one H on each carbon) on a ring system, examples of such moieties include methylene dioxy, ethylenedioxy, —C(CH₃)₂— and the like that form moieties such as, for example:

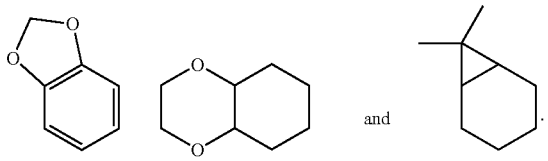

"Ring system substituent" also means a cyclic ring of 3 to 7 ring atoms, wherein 1-2 ring atoms can be heteroatoms, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

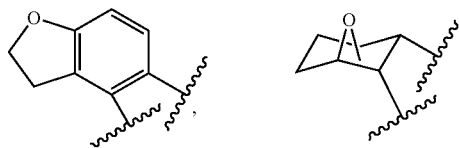

and the like

It should be noted that in hetero-atom containing heterocyclyl ring systems of this invention, there are no hydroxyl groups on carbon atoms adjacent to a N, O or S, as well as there are no N or S groups on carbon adjacent to another heteroatom, Thus, for example, in the ring:

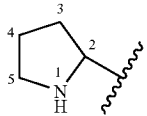

there is no —OH attached directly to carbons marked 2 and 5.

It should also be noted that tautomeric forms such as, for example, the moieties:

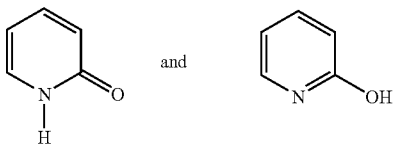

are considered equivalent in certain embodiments of this invention.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., $R^1$, $R^2$, etc.) occurs more than one time in any constituent or in Formula 1.0, its definition on each occurrence is independent of its definition at every other occurrence.

N-oxides can form on a tertiary nitrogen present in an R substituent, or on =N— in a heteroaryl ring substituent and are included in the compounds of formula 1.

The term "prodrug," as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein, the term "composition" is intended to encompass a product comprising the specified ingredients in the specified amounts, as well as any product which results, directly or indirectly, from combination of the specified ingredients in the specified amounts.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Solvate" means a physical association of a compound of this invention with one or more solvent molecules; This physical association involves varying degrees of ionic and covalent bonding, including hydrogen bonding; In certain instances the solvate will be capable of isolation, for example when one or more solvent molecules are incorporated in the crystal lattice of the crystalline solid; "Solvate" encompasses both solution-phase and isolatable solvates; Non-limiting examples of suitable solvates include ethanolates, methanolates, and the like; "Hydrate" is a solvate wherein the solvent molecule is $H_2O$.

Also, as used herein, with reference to chemical structures or formulas, "Bn" represents benzyl, "Et" represents ethyl, "Me" represents methyl, and "Ph' represents phenyl.

Lines drawn into the ring systems indicate that the indicated bond may be attached to any of the substitutable ring carbon atoms. Unless indicated otherwise, when more than one ring is present the bond can be to any of the substitutable ring carbon atoms in any of the rings.

Those skilled in the art will appreciate that formula showing a bond without a terminal group represents a methyl bonded to that position. For example:

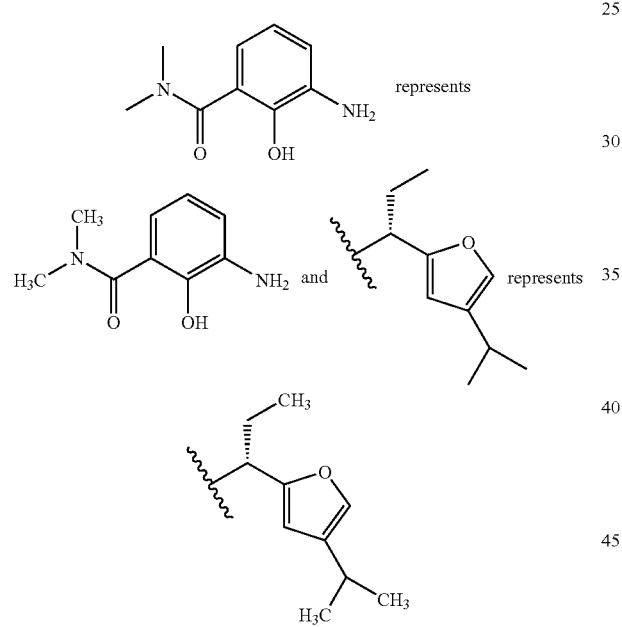

The novel compounds of this invention are compounds of formula 1.0:

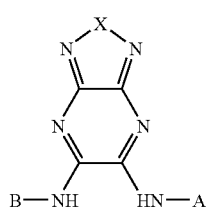
(1.0)

and the pharmaceutically acceptable salts (e.g., sodium or calcium salt) thereof, wherein:

X is O or S (preferably O);

A is selected from the group consisting of:

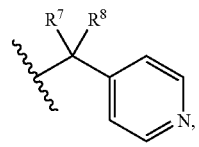
A1

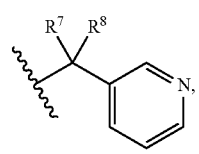
A2

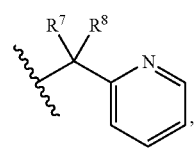
A3

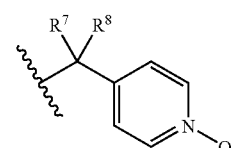
A4

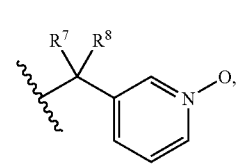
A5

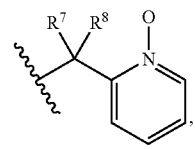
A6

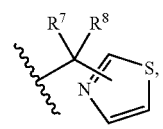
A7

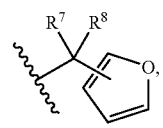
A8

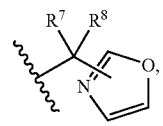
A9

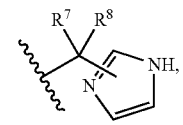
A10

-continued
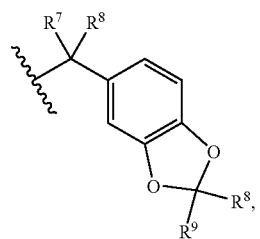 A11
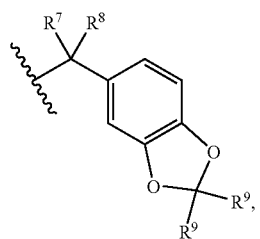 A12
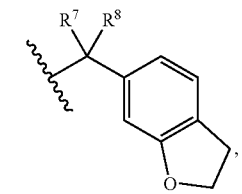 A13
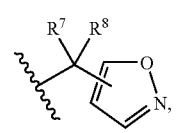 A14
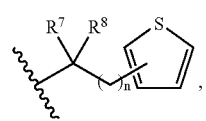 A15
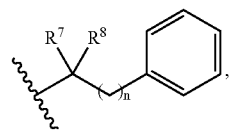 A16
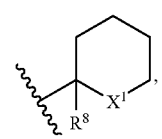 A17
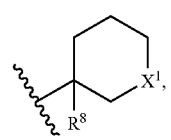 A18
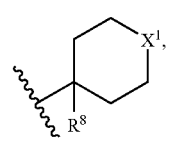 A19
-continued
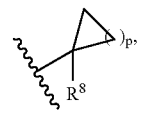 A20
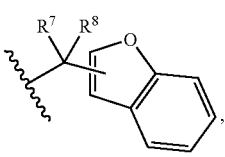 A21
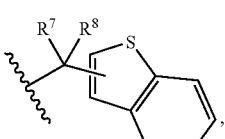 A22
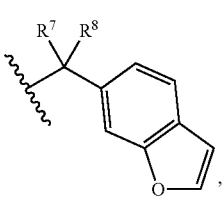 A23
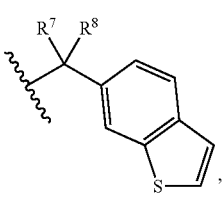 A24
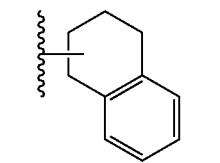 A25
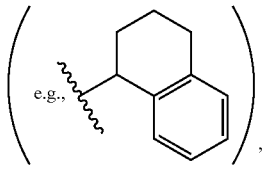 A25.1
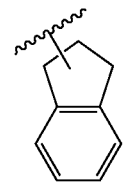 A26
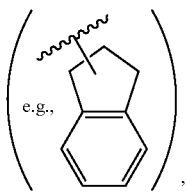 A26.1

-continued

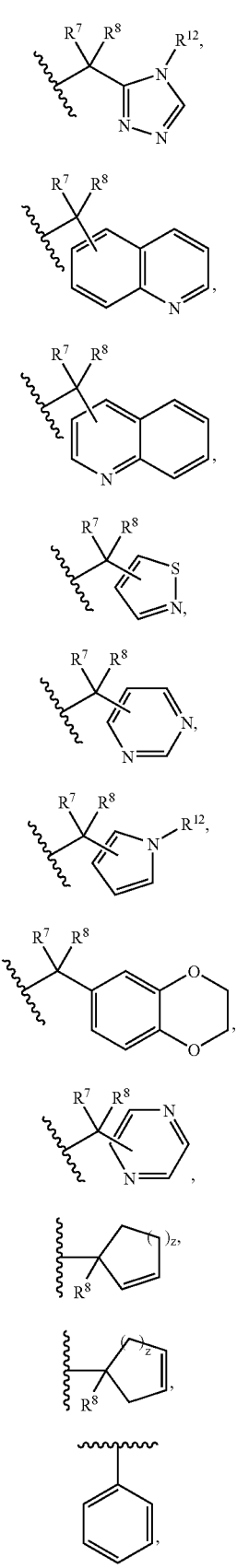

A27
A28
A29
A30
A31
A32
A33
A34
A35
A36
A37

-continued

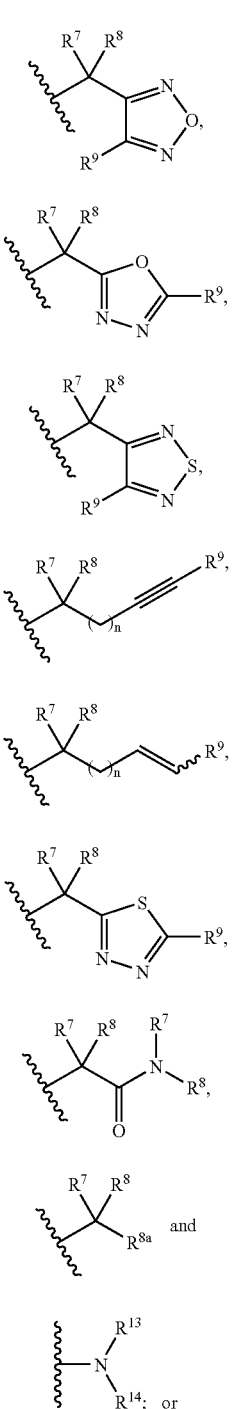

A38
A39
A40
A41
A42
A43
A44
A45
A46

A is a group selected from the group consisting of A1, A2, A3, A4, A5, A6, A7, A8, A9, A10, A13, A14, A15, A16, A17, A18, A19, A20, A21, A22, A23, A24, A25 (e.g., A25.1), A26 (e.g., A26.1), A27, A28, A29, A30, A31, A32, A33, A34, A35, A36 and A37 (as defined above) wherein said A group is substituted with 1 to 6 independently selected $R^9$ groups; or A is a group selected from the group consisting of: A11 and A12 (as defined above) wherein said A group is substituted with 1 to 3 independently selected $R^9$ groups;

B is selected from the group consisting of:
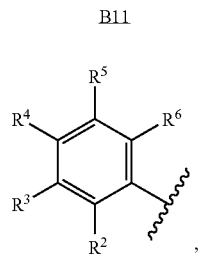
B11
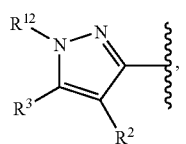
B2
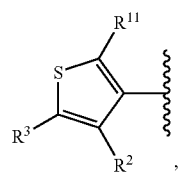
B3
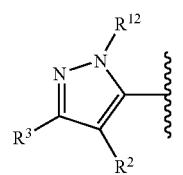
B4
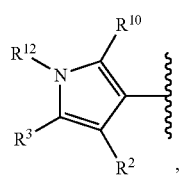
B5
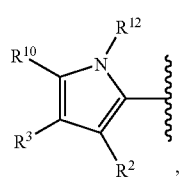
B6
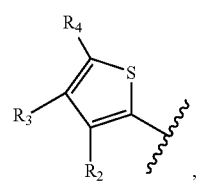
B7
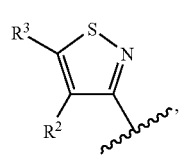
B8
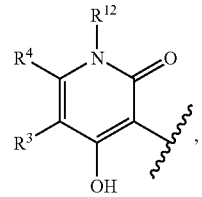
B1
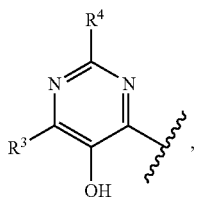
B9
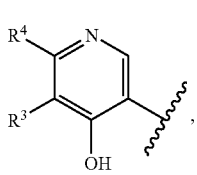
B10
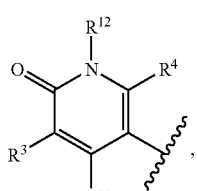
B11
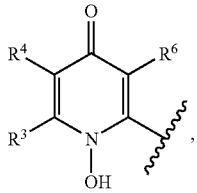
B12
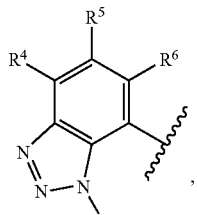
B13
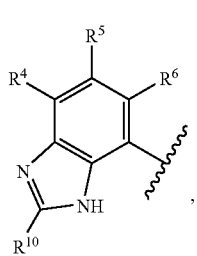
B14

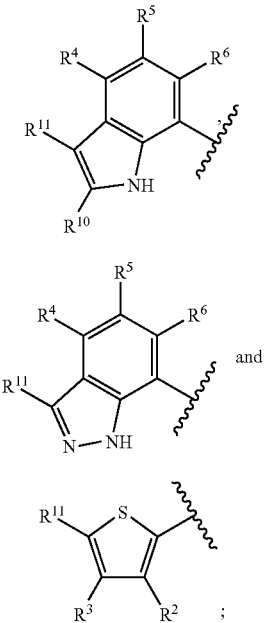

n is 0 to 6;
p is 1 to 5;
X¹ is O, NH, or S;
Z is 1 to 3;
R² is selected from the group consisting of: hydrogen, OH, —C(O)OH, —SH, —SO₂NR¹³R¹⁴, —NHC(O)R¹³, —NHSO₂NR¹³R¹⁴, —NHSO₂R¹³, —NR¹³R¹⁴, —C(O)NR¹³R¹⁴, —C(O)NHOR¹³, —C(O)NR¹³OH, —S(O₂)OH, —OC(O)R¹³, an unsubstituted heterocyclic acidic functional group, and a substituted heterocyclic acidic functional group; wherein there are 1 to 6 substituents on said substituted heterocyclic acidic functional group each substituent being independently selected from the group consisting of: R⁹ groups;

each R³ and R⁴ is independently selected from the group consisting of: hydrogen, cyano, halogen, alkyl, alkoxy, —OH, —CF₃, —OCF₃, —NO₂, —C(O)R¹³, —C(O)OR¹³, —C(O)NHR¹⁷, —C(O)NR¹³R¹⁴, —SO₍ₜ₎NR¹³R¹⁴, —SO(t)R¹³, —C(O)NR¹³OR¹⁴, unsubstituted or substituted aryl, unsubstituted or substituted heteroaryl,

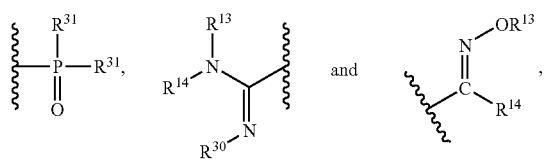

wherein there are 1 to 6 substituents on said substituted aryl group and each substituent is independently selected from the group consisting of: R⁹ groups; and wherein there are 1 to 6 substituents on said substituted heteroaryl group and each substituent is independently selected from the group consisting of: R⁹ groups;

each R⁵ and R⁶ are the same or different and are independently selected from the group consisting of hydrogen, halogen, alkyl, alkoxy, —CF₃, —OCF₃, —NO₂, —C(O)R¹³, —C(O)OR¹³, —C(O)NR¹³R¹⁴, —SO₍ₜ₎NR¹³R¹⁴, —C(O) NR¹³OR¹⁴, cyano, unsubstituted or substituted aryl, and unsubstituted or substituted heteroaryl group; wherein there are 1 to 6 substituents on said substituted aryl group and each substituent is independently selected from the group consisting of: R⁹ groups; and wherein there are 1 to 6 substituents on said substituted heteroaryl group and each substituent is independently selected from the group consisting of: R⁹ groups;

each R⁷ and R⁸ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, —CO₂R¹³, —CONR¹³R¹⁴, alkynyl, alkenyl, and cycloalkenyl; and wherein there are one or more (e.g., 1 to 6) substituents on said substituted R⁷ and R⁸ groups, wherein each substituent is independently selected from the group consisting of: a) halogen, b) —CF₃, c) —COR¹³, d) —OR¹³, e) —NR¹³R¹⁴, f) —NO₂, g) —CN, h) —SO₂OR¹³, i) —Si(alkyl)₃, wherein each alkyl is independently selected, j) —Si(aryl)₃, wherein each alkyl is independently selected, k)-(R¹³)₂R¹⁴Si, wherein each R¹³ is independently selected, l) —CO₂R¹³, m) —C(O)NR¹³R¹⁴, n) —SO₂NR¹³R¹⁴, o) —SO₂R¹³, p) —OC(O)R¹³, q) —OC(O)NR¹³R¹⁴, r) —NR¹³C(O)R¹⁴, and s) —NR¹³CO₂R¹⁴; (fluoroalkyl is one non-limiting example of an alkyl group that is substituted with halogen);

R⁸ᵃ is selected from the group consisting of: hydrogen, alkyl, cycloalkyl and cycloalkylalkyl;

each R⁹ is independently selected from the group consisting of: a) —R¹³, b) halogen, c) —CF₃, d) —COR¹³, e) —OR¹³, f) —NR¹³R¹⁴, g) —NO₂, h) —CN, i) —SO₂R¹³, j) —SO₂NR¹³R¹⁴, k) —NR¹³COR¹⁴, l) —CONR¹³R¹⁴, m) —NR¹³CO₂R¹⁴, n) —CO₂R¹³, o) 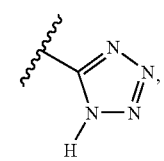

p) alkyl substituted with one or more (e.g., one) —OH groups (e.g., —(CH₂)qOH, wherein q is 1-6, usually 1 to 2, and preferably 1), q) alkyl substituted with one or more (e.g., one) —NR¹³R¹⁴ group (e.g., —(CH₂)qNR¹³R¹⁴, wherein q is 1-6, usually 1 to 2, and preferably 1), and r) —N(R¹³)SO₂R¹⁴ (e.g., R¹³ is H and R¹⁴ is alkyl, such as methyl);

each R¹⁰ and R¹¹ is independently selected from the group consisting of R¹³, hydrogen, alkyl (e.g., C₁ to C₆, such as methyl), halogen, —CF₃, —OCF₃, —NR¹³R¹⁴, —NR¹³C(O)NR¹³R¹⁴, —OH, —C(O)OR¹³, —SH, —SO₍ₜ₎NR¹³R¹⁴, —SO₂R¹³, —NHC(O)R¹³, —NHSO₂NR¹³R¹⁴, —NHSO₂R¹³, —C(O)NR¹³R¹⁴, —C(O)NR¹³OR¹⁴, —OC(O)R¹³ and cyano;

R¹² is selected from the group consisting of: hydrogen, —C(O)OR¹³, unsubstituted or substituted aryl, unsubstituted or substituted heteroaryl, unsubstituted or substituted arylalkyl, unsubstituted or substituted cycloalkyl, unsubstituted or substituted alkyl, unsubstituted or substituted cycloalkylalkyl, and unsubstituted or substituted heteroarylalkyl group; wherein there are 1 to 6 substituents on the substituted R¹² groups and each substituent is independently selected from the group consisting of: R⁹ groups;

each $R^{13}$ and $R^{14}$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, unsubstituted or substituted heterocyclic, unsubstituted or substituted fluoroalkyl, and unsubstituted or substituted heterocycloalkylalkyl (wherein "heterocyloalkyl" means heterocyclic); wherein there are 1 to 6 substituents on said substituted $R^{13}$ and $R^{14}$ groups and each substituent is independently selected from the group consisting of: alkyl, —$CF_3$, —OH, alkoxy, aryl, arylalkyl, fluroalkyl, cycloalkyl, cycloalkylalkyl, heteroaryl, heteroarylalkyl, —$N(R^{40})_2$, —$C(O)OR^{15}$, —$C(O)NR^{15}R^{16}$, —$S(O)_tNR^{15}R^{16}$, —$C(O)R^{15}$, —$SO_2R^{15}$ provided that $R^{15}$ is not H, halogen, and —$NHC(O)NR^{15}R^{16}$; or $R^{13}$ and $R^{14}$ taken together with the nitrogen they are attached to in the groups —$C(O)NR^{13}R^{14}$ and —$SO_2NR^{13}R^{14}$ form an unsubstituted or substituted saturated heterocyclic ring (preferably a 3 to 7 membered heterocyclic ring), said ring optionally containing one additional heteroatom selected from the group consisting of: O, S and $NR^{18}$; wherein there are 1 to 3 substituents on the substituted cyclized $R^{13}$ and $R^{14}$ groups (i.e., there is 1 to 3 substituents on the ring formed when the $R^{13}$ and $R^{14}$ groups are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —$C(O)OR^{15}$, —$C(O)NR^{15}R^{16}$, —$SO_tNR^{15}R^{16}$, —$C(O)R^{15}$, —$SO_2R^{15}$ provided that $R^{15}$ is not H, —$NHC(O)NR^{15}R^{16}$, —$NHC(O)OR^{15}$, halogen, and a heterocylcoalkenyl group (i.e., a heterocyclic group that has at least one, and preferably one, double bond in a ring, e.g.,

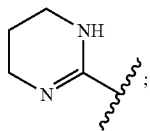

each $R^{15}$ and $R^{16}$ is independently selected from the group consisting of: H, alkyl, aryl, arylalkyl, cycloalkyl and heteroaryl;

$R^{17}$ is selected from the group consisting of: —$SO_2$alkyl, —$SO_2$aryl, —$SO_2$cycloalkyl, and —$SO_2$heteroaryl;

$R^{18}$ is selected from the group consisting of: H, alkyl, aryl, heteroaryl, —$C(O)R^{19}$, —$SO_2R^{19}$ and —$C(O)NR^{19}R^{20}$;

each $R^{19}$ and $R^{20}$ is independently selected from the group consisting of: alkyl, aryl and heteroaryl;

$R^{30}$ is selected from the group consisting of: alkyl, cycloalkyl, —CN, —$NO_2$, or —$SO_2R^{15}$ provided that $R^{15}$ is not H;

each $R^{31}$ is independently selected from the group consisting of: unsubstituted alkyl, unsubstituted or substituted aryl, unsubstituted or substituted heteroaryl and unsubstituted or substituted cycloalkyl; wherein there are 1 to 6 substituents on said substituted $R^{31}$ groups and each substituent is independently selected from the group consisting of: alkyl, halogen, and —$CF_3$;

each $R^{40}$ is independently selected from the group consisting of: H, alkyl and cycloalkyl; and t is 0, 1 or 2.

Representative embodiments of this invention are described below. The embodiments have been numbered for purposes of reference thereto.

Embodiment No. 1 is directed to the compounds of formula 1.0 wherein B is selected from the group consisting of B1 to B18 (as defined above for formula 1.0), wherein for B1 the substitutent $R^3$ is selected from the group consisting of: —$C(O)NR^{13}R^{14}$,

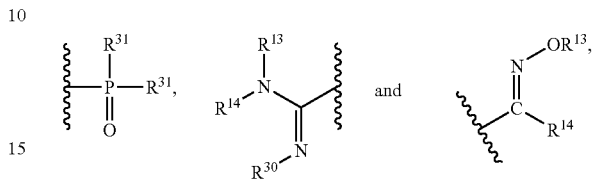

and all other substitutents are as defined for formula 1.0.

Embodiment No. 2 is directed to the compounds of formula 1.0 wherein B is selected from the group consisting of B1 to B7 (as defined above for formula 1.0), wherein for B1 the substitutent $R^3$ is selected from the group consisting of: —$C(O)NR^{13}R^{14}$,

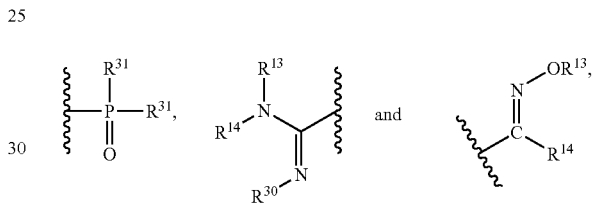

and all other substitutents are as defined for formula 1.0.

Embodiment No. 3 is directed to the compounds of formula 1.0 wherein B is B1 (as defined above for formula 1.0) and $R^3$ for B1 is selected from the group consisting of: —$C(O)NR^{13}R^{14}$,

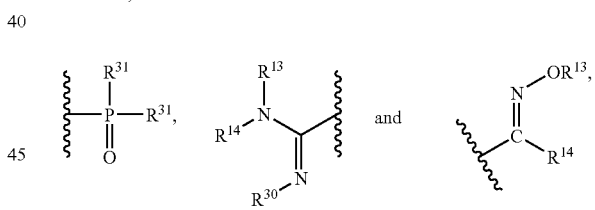

and all other substituents are as defined in formula 1.0.

Embodiment No. 4 is directed to the compounds of formula 1.0 wherein B is B1 of the formula B1.1:

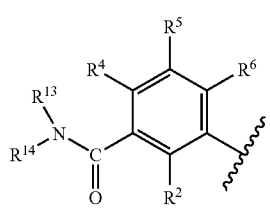

and all other substituents are as defined in formula 1.0.

Embodiment No. 5 is directed to the compounds of formula 1.0 wherein B is B1.1, as defined in Embodiment No. 4, and $R^{13}$ and $R^{14}$ in said B1.1 are each the same or different alkyl group, and all other substituents are as defined in formula 1.0.

Embodiment No. 6 is directed to the compounds of formula 1.0 wherein B is B1.1, as defined in Embodiment No. 4, and (1) $R^2$ is —OH, and all other substituents are as defined in formula 1.0, or (2) $R^2$ is —OH and $R^{13}$ and $R^{14}$ are each the same or different alkyl group, and all other substituents are as defined in formula 1.0.

Embodiment No. 7 is directed to the compounds of formula 1.0 wherein B is B1, as defined for formula 1.0, and $R^3$ for said B1 is selected from the group consisting of:

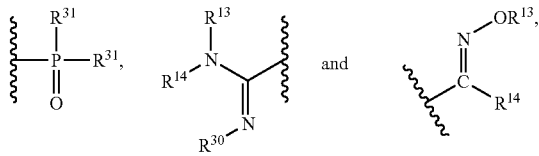

and all other substituents are as defined in formula 1.0.

Embodiment No. 8 is directed to the compounds of formula 1.0 wherein B is B1, as defined for formula 1.0, $R^3$ for said B1 is selected from the group consisting of:

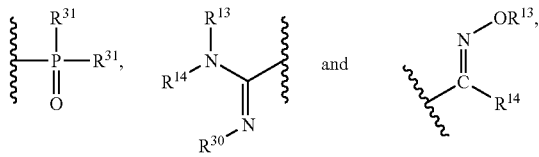

$R^2$ for said B1 is —OH, and all other substituents are as defined in formula 1.0.

Embodiment No. 9 is directed to compounds of formula 1.0 wherein B is B1 of the formula B1.2:

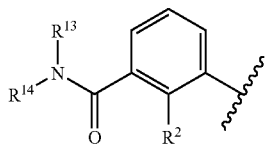

B1.2 wherein $R^2$, $R^{13}$, and $R^{14}$ for said B1.2 are as defined for compounds of formula 1.0, and all other substituents are as defined in formula 1.0.

Embodiment No. 10 is directed to the compounds of formula 1.0 wherein B is B1.2, as defined in Embodiment No. 9, and $R^2$ for B1.2 is —OH, $R^{13}$ and $R^{14}$ for B1.2 are as defined for compounds of formula 1.0, and all other substituents are as defined in formula 1.0.

Embodiment No. 11 is directed to the compounds of formula 1.0 wherein B is B1.2, as defined in Embodiment No 9, and $R^2$ for B1.2 is as defined for the compounds of formula 1.0, $R^{13}$ and $R^{14}$ for B1.2 are the same or different alkyl group, and all other substituents areas defined for compounds of formula 1.0.

Embodiment No. 12 is directed to the compounds of formula 1.0 wherein B is B1.2, as defined in Embodiment No. 9, and $R^2$ for B1.2 is —OH, $R^{13}$ and $R^{14}$ for B1.2 are the same or different alkyl group, and all other substituents are as defined for the compounds of formula 1.0.

Embodiment No. 13 is directed to the compounds of formula 1.0 wherein B is as described in Embodiment No. 7, $R^4$ is H, $R^5$ is H, $R^6$ is H, and all other substituents areas defined for the compounds of formula 1.0.

Embodiment No. 14 is directed to the compounds of formula 1.0 wherein B is as described in Embodiment No. 7, $R^4$ is H, $R^5$ is H, $R^6$ is H, and all other substituents areas defined for the compounds of formula 1.0.

Embodiment No. 15 is directed to the compounds of formula 1.0 wherein B is as described in Embodiments Nos. 5, 6, 9 and 10, except that $R^{13}$ and $R^{14}$ are each methyl, and all other substituents are as defined in formula 1.0.

Embodiment No. 16 is directed to the compounds of formula 1.0 wherein B is selected from the group consisting of groups B2, B3, B4, B5 and B6, as defined for formula 1.0, and all other substituents are as defined for formula 1.0.

Embodiment No. 17 is directed to the compounds of formula 1.0 wherein B is B3, as defined for formula 1.0, and all other substituents are as defined for formula 1.0.

Embodiment No. 18 is directed to the compounds of formula 1.0 wherein B is B3, as defined for formula 1.0, :$R^{11}$ for B3 is H, and all other substituents are as defined in formula 1.0.

Embodiment No. 19 is directed to the compounds of formula 1.0 wherein B is B3, as defined for formula 1.0, and: $R^2$ for B3 is —OH, and all other substituents are as defined in formula 1.0.

Embodiment No. 20 is directed to the compounds of formula 1.0 wherein B is B3, as defined for formula 1.0, $R^3$ for B3 is —C(O)NR$^{13}$R$^{14}$, and all other substituents are as defined in formula 1.0.

Embodiment No. 21 is directed to the compounds of formula 1.0 wherein B is B3, as defined for formula 1.0, $R^3$ for B3 is —S(O)$_t$NR$^{13}$R$^{14}$ (e.g., t is 2), and all other substituents are as defined in formula 1.0.

Embodiment No. 22 is directed to the compounds of formula 1.0 wherein B is B3, as defined in formula 1.0, $R^2$ for B3 is —OH, $R^3$ for B3 is —C(O)NR$^{13}$R$^{14}$, and all other substituents are as defined in formula 1.0.

Embodiment No. 23 is directed to the compounds of formula 1.0 wherein B is B3, as defined for formula 1.0, $R^2$ for B3 is —OH, and $R^3$ for B3 is —S(O)$_t$NR$^{13}$R$^{14}$ (e.g., t is 2), and all other substituents are as defined in formula 1.0.

Embodiment No. 24 is directed to the compounds of formula 1.0 wherein B is B3, as defined for formula 1.0, $R^2$ for B3 is —OH, $R^3$ for B3 is —C(O)NR$^{13}$R$^{14}$, $R^{11}$ for B3 is H, and all other substituents are as defined in formula 1.0.

Embodiment No. 25 is directed to the compounds of formula 1.0 wherein B is B3, as defined for formula 1.0, $R^3$ for B3 is —S(O)$_t$NR$^{13}$R$^{14}$ (e.g., t is 2), each $R^{13}$ and $R^{14}$ for B3 are the same or different and are selected from the group consisting of: H and alkyl (e.g., methyl, ethyl, isopropyl and t-butyl). In this embodiment, each $R^{13}$ and $R^{14}$ for B3 are generally selected from the group consisting of: H and ethyl, and preferably $R^{13}$ and $R^{14}$ for B3 are ethyl, and all other substituents are as defined in formula 1.0.

Embodiment No. 26 is directed to the compounds of formula 1.0 wherein B is B3, as defined for formula 1.0, $R^3$ for B3 is —S(O)$_t$NR$^{13}$R$^{14}$ (e.g., t is 2), $R^{11}$ for B3 is H, and each $R^{13}$ and $R^{14}$ for B3 are the same or different and are selected from the group consisting of: H and alkyl (e.g., methyl, ethyl, isopropyl and t-butyl). In this embodiment, each $R^{13}$ and $R^{14}$ for B3 are generally selected from the group consisting of: H and ethyl, and preferably $R^{13}$ and $R^{14}$ for B3 are ethyl, and all other substituents are as defined in formula 1.0.

Embodiment No. 27 is directed to the compounds of formula 1.0 wherein B is B3, as defined for formula 1.0, $R^2$ for B3 is —OH, $R^3$ for B3 is —S(O)$_t$NR$^{13}$R$^{14}$ (e.g., t is 2), $R^{11}$ for B3 is H, and all other substituents are as defined in formula 1.0.

Embodiment No. 28 is directed to the compounds of formula 1.0 wherein B is B3, as defined for formula 1.0, $R^2$ for B3 is —OH, $R^3$ for B3 is —C(O)NR$^{13}$R$^{14}$, $R^{11}$ for B3 is H, and $R^{13}$ and $R^{14}$ for B3 are independently selected from the group consisting of: alkyl, unsubstituted heteroaryl and substituted heteroaryl, and all other substituents are as defined in formula 1.0. In general, one of $R^{13}$ or $R^{14}$ for B3 is alkyl (e.g., methyl). An example of a substituted heteroaryl group is

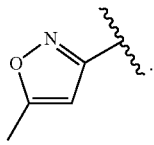

Embodiment No. 29 is directed to the compounds of formula 1.0 wherein B is B3, as defined for formula 1.0, $R^2$ for B3 is —OH, $R^3$ for B3 is —S(O)$_t$NR$^{13}$R$^{14}$ (e.g., t is 2), $R^{11}$ for B3 is H, and each $R^{13}$ and $R^{14}$ for B3 are the same or different and are selected from the group consisting of: H and alkyl (e.g., methyl, ethyl, isopropyl and t-butyl), and all other substituents are as defined in formula 1.0. In this embodiment, each $R^{13}$ and $R^{14}$ for B3 are generally selected from the group consisting of: H and ethyl, and preferably $R^{13}$ and $R^{14}$ for B3 are ethyl.

Embodiment No. 30 is directed to the compounds of formula 1.0 wherein B is B7, as defined for formula 1.0, and all other substituents are as defined in formula 1.0.

Embodiment No. 31 is directed to the compounds of formula 1.0 wherein B is B8, as defined for formula 1.0, and all other substituents are as defined in formula 1.0.

Embodiment No. 32 is directed to the compounds of formula 1.0 wherein B is selected from the group consisting of:

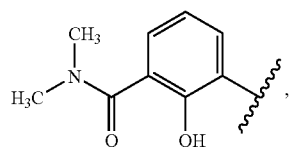
B1.3

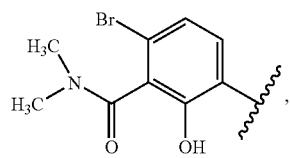
B1.4

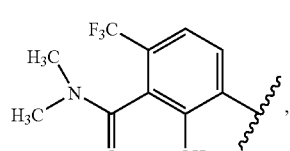
B1.5

-continued

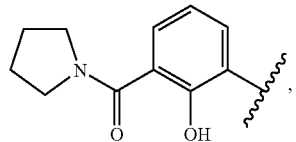
B1.6

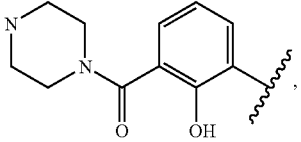
B1.7

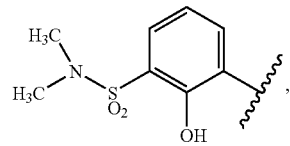
B1.8

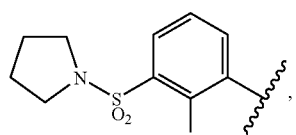
B1.9

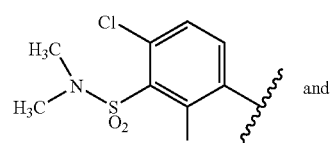
B1.10
and

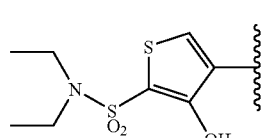
B3.1

Embodiment No. 33 is directed to the compounds of formula 1.0 wherein B is selected from the group consisting of: B1.3, B1.4 and B1.5, as defined in Embodiment No. 32.

Embodiment No. 34 is directed to the compounds of formula 1.0 wherein B is B1.3, as defined in Embodiment No. 32.

Embodiment No. 35 is directed to the compounds of formula 1.0 wherein B is selected from the group consisting of: B1.6 and B1.7, as defined in Embodiment No. 32.

Embodiment No. 36 is directed to the compounds of formula 1.0 wherein B is selected from the group consisting of: B1.8 and B1.10, as defined in Embodiment No. 32.

Embodiment No. 37 is directed to the compounds of formula 1.0 wherein B is B1.9, as defined in Embodiment No. 32.

Embodiment No. 38 is directed to the compounds of formula 1.0 wherein B is B3.1, as defined in Embodiment No. 32.

Embodiment No. 39 is directed to compounds of formula 1.0 wherein B is selected from the group consisting of: B1, B14, B15, B16, and B17, as defined in formula 1.0.

Embodiment No. 40 is directed to compounds of formula 1.0 wherein B is B1, as defined in formula 1.0, $R^2$, $R^4$, $R^5$ and $R^6$ for B1 are as defined for formula 1.0; and $R^3$ for B1 is selected from the group consisting of: hydrogen, cyano, halogen, alkyl, alkoxy, —OH, —CF$_3$, —OCF$_3$, —NO$_2$, —C(O)R$^{13}$, —C(O)OR$^{13}$, —C(O)NHR$^{17}$, —SO$_{(t)}$NR$^{13}$R$^{14}$, —SO$_{(t)}$ $R^{13}$, —C(O)NR$^{13}$OR$^{14}$, unsubstituted or substituted aryl, unsubstituted or substituted heteroaryl, wherein there are 1 to 6 substituents on said substituted aryl group and each substituent is independently selected from the group consisting of: $R^9$ groups; and wherein there are 1 to 6 substituents on said substituted heteroaryl group and each substituent is independently selected from the group consisting of: $R^9$ groups.

Embodiment No. 41 is directed to compounds of formula 1.0 wherein B is selected from the group consisting of: B1, B2, B3, B4, B5, B10, B11, B12, B13, B14, B15, B16, and B17, as defined for formula 1.0.

Embodiment No. 42 is directed to compounds of formula 1.0 wherein B is selected from the group consisting of: B1, B2, B3, B4, B5, and B14, and wherein for said B groups:

$R^2$ is selected from the group consisting of: H, OH, —NHC(O)R$^{13}$ or and —NHSO$_2$R$^{13}$;

$R^3$ is selected from the group consisting of: —SO$_2$NR$^{13}$R$^{14}$, —NO$_2$, cyano, —C(O)NR$^{13}$R$^{14}$, —SO$_2$R$^{13}$; and —C(O)OR$^{13}$;

$R^4$ is selected from the group consisting of: H, —NO$_2$, cyano, —CH$_3$, halogen, and —CF$_3$;

$R^5$ is selected from the group consisting of: H, —CF$_3$, —NO$_2$, halogen and cyano;

$R^6$ is selected from the group consisting of: H, alkyl and —CF$_3$;

each $R^{10}$ and $R^{11}$ is independently selected from the group consisting of: hydrogen, halogen, —CF$_3$, —NR$^{13}$R$^{14}$, —NR$^{13}$C(O)NR$^{13}$R$^{14}$, —C(O)OR$^{13}$, —SH, —SO$_{(t)}$NR$^{13}$R$^{13}$R$^{14}$, —SO$_2$R$^{13}$, —NHC(O)R$^{13}$, —NHSO$_2$NR$^{13}$R$^{14}$, —NHSO$_2$R$^{13}$, —C(O)NR$^{13}$R$^{14}$, —C(O)NR$^{13}$OR$^{14}$—OC(O)R$^{13}$, —COR$^{13}$, —OR$^{13}$, and cyano;

each $R^{13}$ and $R^{14}$ is independently selected from the group consisting of: H, methyl, ethyl, isopropyl and t-butyl; or $R^{13}$ and $R^{14}$ when taken together with the nitrogen they are attached to in the groups —NR$^{13}$R$^{14}$, —C(O)NR$^{13}$R$^{14}$, —SO$_2$NR$^{13}$R$^{14}$, —OC(O)NR$^{13}$R$^{14}$, —CONR$^{13}$R$^{14}$, —NR$^{13}$C(O)NR$^{13}$R$^{14}$, —SO$_t$NR$^{13}$R$^{14}$, —NHSO$_2$NR$^{13}$R$^{14}$ form an unsubstituted or substituted saturated heterocyclic ring (preferably a 3 to 7 membered ring) optionally having one additional heteroatom selected from the group consisting of: O, S or NR$^{13}$; wherein R$^{18}$ is selected from the group consisting of: H, alkyl, aryl, heteroaryl, —C(O)R$^{19}$, —SO$_2$R$^{19}$ and —C(O)NR$^{19}$R$^{20}$; wherein each R$^{19}$ and R$^{20}$ is independently selected from the group consisting of: alkyl, aryl and heteroaryl; wherein there are 1 to 3 substituents on the substituted cyclized R$^{13}$ and R$^{14}$ groups (i.e., the substituents on the ring formed when R$^{13}$ and R$^{14}$ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR$^{15}$, —C(O)NR$^{15}$R$^{16}$, —SO$_t$NR$^{15}$R$^{16}$, —C(O)R$^{15}$, —SO$_2$R$^{15}$ provided that R$^{15}$ is not H, —NHC(O)NR$^{15}$R$^{16}$ and halogen; and wherein each R$^{15}$ and R$^{16}$ is independently selected from the group consisting: of H, alkyl, aryl, arylalkyl, cycloalkyl and heteroaryl.

Embodiment No. 43 is directed to compounds of formula 1.0 wherein B is selected from the group consisting of: B1 and B3, and wherein for said B groups:

$R^2$ is selected from the group consisting of: H, OH, —NHC(O)R$^{13}$ and —NHSO$_2$R$^{13}$;

$R^3$ is selected from the group consisting of: —C(O)NR$^{13}$R$^{14}$, —SO$_2$NR$^{13}$R$^{14}$, —NO$_2$, cyano, —SO$_2$R$^{13}$; and —C(O)OR$^{13}$;

$R^4$ is selected from the group consisting of: H, —NO$_2$, cyano, —CH$_3$ or —CF$_3$;

$R^5$ is selected from the group consisting of: H, —CF$_3$, —NO$_2$, halogen and cyano; and $R^6$ is selected from the group consisting of: H, alkyl and —CF$_3$;

$R^{11}$ is selected from the group consisting of: H, halogen and alkyl; and each $R^{13}$ and $R^{14}$ is independently selected from the group consisting of: H, methyl, ethyl, isopropyl and t-butyl; or $R^{13}$ and $R^{14}$ when taken together with the nitrogen they are attached to in the groups —NR$^{13}$R$^{14}$, —C(O)NR$^{13}$R$^{14}$, —SO$_2$NR$^{13}$R$^{14}$, —OC(O)NR$^{13}$R$^{14}$, —CONR$^{13}$R$^{14}$, —NR$^{13}$C(O)NR$^{13}$R$^{14}$, —SO$_t$NR$^{13}$R$^{14}$, —NHSO$_2$NR$^{13}$R$^{14}$ form an unsubstituted or substituted saturated heterocyclic ring (preferably a 3 to 7 membered ring) optionally having one additional heteroatom selected from O, S or NR$^{18}$ wherein R$^{18}$ is selected from H, alkyl, aryl, heteroaryl, —C(O)R$^{19}$, —SO$_2$R$^{19}$ and —C(O)NR$^{19}$R$^{20}$, wherein each R$^{19}$ and R$^{20}$ is independently selected from alkyl, aryl and heteroaryl, wherein there are 1 to 3 substituents on the substituted cyclized R$^{13}$ and R$^{14}$ groups (i.e., on the ring formed when R$^{13}$ and R$^{14}$ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR$^{15}$, —C(O)NR$^{15}$R$^{16}$, —SO$_t$NR$^{15}$R$^{16}$, —C(O)R$^{15}$, —SO$_2$R$^{15}$ provided that R$^{15}$ is not H, —NHC(O)NR$^{15}$R$^{16}$ and halogen; and wherein each R$^{15}$ and R$^{16}$ is independently selected from the group consisting of: H, alkyl, aryl, arylalkyl, cycloalkyl and heteroaryl.

Embodiment No. 44 is directed to compounds of formula 1.0 wherein B is selected from the group consisting of: B1 and B3, and wherein for said B groups:

$R^2$ is selected from the group consisting of: H, OH, —NHC(O)R$^{13}$ and —NHSO$_2$R$^{13}$;

$R^3$ is selected from the group consisting of: —C(O)NR$^{13}$R$^{14}$—SO$_2$NR$^{13}$R$^{14}$, —NO$_2$, cyano, and —SO$_2$R$^{13}$;

$R^4$ is selected from the group consisting of: H, —NO$_2$, cyano, —CH$_3$ or —CF$_3$;

$R^5$ is selected from the group consisting of: H, —CF$_3$, —NO$_2$, halogen and cyano; and $R^6$ is selected from the group consisting of: H, alkyl and —CF$_3$;

$R^{11}$ is selected from the group consisting of: H, halogen and alkyl; and each $R^{13}$ and $R^{14}$ is independently selected from the group consisting of: methyl and ethyl.

Embodiment No. 45 is directed to compounds of formula 1.0 wherein B is selected from the group consisting of: B1 and B3, and wherein for said B groups:

$R^2$ is —OH;

$R^3$ is selected from the group consisting of: —SO$_2$NR$^{13}$R$^{14}$ and —CONR$^{13}$R$^{14}$;

$R^4$ is selected form the group consisting of: H, —CH$_3$ and —CF$_3$;

$R^5$ is selected from the group consisting of: H and cyano;

$R^6$ is selected from the group consisting of: H, —CH$_3$ and —CF$_3$;

$R^{11}$ is H; and $R^{13}$ and $R^{14}$ are methyl.

Embodiment No. 46 is directed to compounds of formula 1.0 wherein A is selected from the group consisting of: A1, A2, A3, A4, A5, A6, A8, A9, A11, A14, A15, A16, A20, A41, A42 and A45, as defined for formula 1.0, wherein said A1, A2, A3, A4, A5, A6, A8, A9, A11, A14, A15, A16 and A20 groups are substituted or unsubstituted as defined for formula 1.0, and wherein each $R^7$ and $R^8$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, —$CO_2R^{13}$, —$CONR^{13}R^{14}$, fluoroalkyl, alkynyl, alkenyl, and cycloalkenyl, wherein said substituents on said $R^7$ and $R^8$ substituted groups are selected from the group consisting of: a) cyano, b) —$CO_2R^{13}$, c) —$C(O)NR^{13}R^{14}$, d) —$SO_2NR^{13}R^{14}$, e) —$NO_2$, f) —$CF_3$, g) —$OR^{13}$, h) —$NR^{13}R^{14}$, i) —$OC(O)R^{13}$, j) —$OC(O)NR^{13}R^{14}$, and k) halogen; and $R^{8a}$ and $R^9$ are as defined in formula 1.0.

Embodiment No. 47 is directed to compounds of formula 1.0 wherein A is selected from the group consisting of: A1, A2, A3, A4, A5, A6, A8, A9, A11, A14, A15, A16, A20, A41, A42 and A45, as defined for formula 1.0, wherein:

said A1, A2, A3, A4, A5, A6, A8, A9, A11, A14, A15, A16, A20 groups are unsubstituted, or are substituted with 1 to 3 substituents independently selected from the group consisting of: halogen, alkyl, cycloalkyl, —$CF_3$, cyano, —$OCH_3$, and —$NO_2$, each $R^7$ and $R^8$ for said A1, A2, A3, A4, A5, A6, A8, A9, A11, A14, A15, A16, A20 groups is independently selected from the group consisting of: H, alkyl (e.g., methyl, ethyl, t-butyl, and isopropyl), fluoroalkyl (such as, —$CF_3$ and —$CF_2CH_3$), cycloalkyl (e.g., cyclopropyl, and cyclohexyl), and cycloalkylalkyl (e.g., cyclopropylmethyl), and $R^9$ for said A1, A2, A3, A4, A5, A6, A8, A9, A11, A14, A15, A16, A20 groups is selected from the group consisting of: H, halogen, alkyl, cycloalkyl, —$CF_3$, cyano, —$OCH_3$, and —$NO_2$, and said $R^7$ and $R^8$ substituents for said A41, A42 and A45 groups are each independently selected from the group consisting of: H, alkyl (e.g., methyl, ethyl, t-butyl, and isopropyl), fluoroalkyl (such as, —$CF_3$ and —$CF_2CH_3$), cycloalkyl (e.g., cyclopropyl, and cyclohexyl), and cycloalkylalkyl (e.g., cyclopropylmethyl); wherein $R^{8a}$ is as defined in formula 1.0, and $R^9$ for said A41, A42 and A45 groups is selected from the group consisting of: H, halogen, alkyl, cycloalkyl, —$CF_3$, cyano, —$OCH_3$, and —$NO_2$.

Embodiment No. 48 is directed to compounds of formula 1.0 wherein A is selected from the group consisting of: A1, A2, A4, A5, A8, A9, A11, A14, A15, A16, A20.1, A20.2 and A45, wherein:

said A1, A2, A4, A5, A8, A9, A11, A14, A15, A16 and A45 groups are as defined for formula 1.0, said A20.1 and A20.2 groups are:

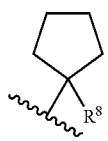

and

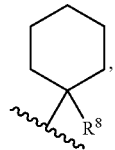

and said A1, A2, A4, A5, A8, A9, A11, A14, A15, A16, A20.1 and A20.2 groups are unsubstituted, or substituted with 1 to 3 substituents independently selected from the group consisting of: H, F, Cl, Br, alkyl, cycloalkyl, and —$CF_3$, $R^7$ is selected from the group consisting of: H, fluoroalkyl, alkyl and cycloalkyl, $R^8$ is selected form the group consisting of: H, alkyl, —$CF_2CH_3$ and —$CF_3$, and $R^9$ is selected from the group consisting of: H, F, Cl, Br, alkyl or —$CF_3$, and said $R^7$ substituent for said A45 group is selected from the group consisting of: H, fluoroalkyl, alkyl and cycloalkyl, $R^8$ for said A45 group is selected form the group consisting of: H, alkyl, —$CF_2CH_3$ and —$CF_3$, and $R^{8a}$ for said A45 group is as defined for formula 1.0.

Embodiment No. 49 is directed to compounds of formula 1.0 wherein A is selected from the group consisting of: A8, A15.1, A16.1, A20.1, A20.2 and A45 wherein:

said A15.1 and A16.1 are

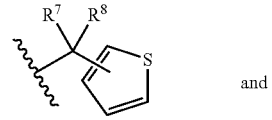

and

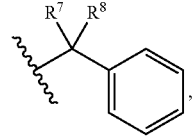

said A20.1 and A20.2 are as defined in Embodiment No. 48, said A45 is as defined for formula 1.0, said A8, A15.1, A16.1, A20.1 and A20.2 groups are unsubstituted, or are substituted with 1 to 3 substituents independently selected from the group consisting of: H, F, Cl, Br, alkyl, cycloalkyl, and —$CF_3$, $R^7$ for said A8, A15.1, A16.1, A20.1 and A20.2 groups is selected from the group consisting of: H, —$CF_3$, —$CF_2CH_3$, methyl, ethyl, isopropyl, cyclopropyl and t-butyl, and $R^8$ for said A8, A15.1, A16.1, A20.1 and A20.2 groups is H said $R^7$ for said A45 group is selected from the group consisting of: H, —$CF_3$, —$CF_2CH_3$, methyl, ethyl, isopropyl, cyclopropyl and t-butyl, and $R^8$ for said A45 group is H, and $R^{8a}$ for said A45 group is as defined for formula 1.0.

Embodiment No. 50 is directed to compounds of formula 1.0 wherein A is selected from the group consisting of: A8, A15.1, A16.1, A20.1, A20.2 and A45, as defined in Embodiment No. 49, wherein:

said A8, A5.1, A16.1, A20.1 and A20.2 groups are unsubstituted, or are substituted with 1 to 3 substituents independently selected from the group consisting of: F, Cl, Br, alkyl, cycloalkyl, and —CF$_3$, R$^7$ for said A8, A15.1, A16.1, A20.1 and A20.2 groups is selected from the group consisting of: H, —CF$_3$, —CF$_2$CH$_3$, methyl, ethyl, isopropyl, cyclopropyl and t-butyl, and R$^8$ for said A8, A15.1, A16.1, A20.1 and A20.2 groups is H, and said R$^7$ for said A45 group is selected from the group consisting of: H, —CF$_3$, —CF$_2$CH$_3$, methyl, ethyl, isopropyl, cyclopropyl and t-butyl, and R$^8$ for said A45 group is H, and R$^{8a}$ for said A45 group is as defined for formula 1.0.

Embodiment No. 51 is directed to compounds of formula 1.0 wherein A is selected from the group consisting of: A8, A11, A15, A16, and A37, and all other substitutents are as defined for formula 1.0.

Embodiment No. 52 is directed to compounds of formula 1.0 wherein A is A11, and all other substitutents are as defined for formula 1.0.

Embodiment No. 53 is directed to compounds of formula 1.0 wherein A is A15, and all other substitutents are as defined for formula 1.0.

Embodiment No. 54 is directed to compounds of formula 1.0 wherein A is A16, and all other substitutents are as defined for formula 1.0.

Embodiment No. 55 is directed to compounds of formula 1.0 wherein A is A37, and all other substitutents are as defined for formula 1.0.

Embodiment No. 56 is directed to compounds of formula 1.0 wherein A is selected from the group consisting of:

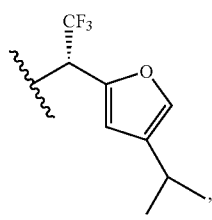
A8.1

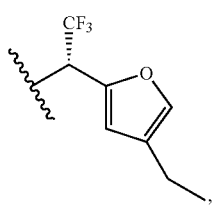
A8.2

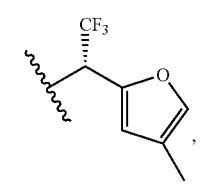
A8.3

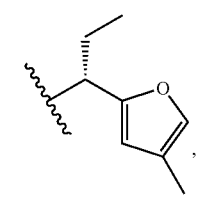
A8.4

-continued

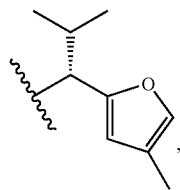
A8.5

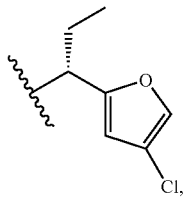
A8.6

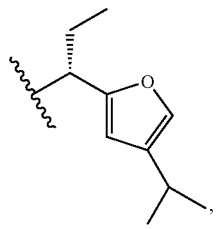
A8.7

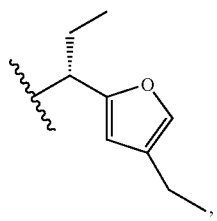
A8.8

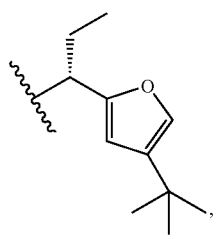
A8.9

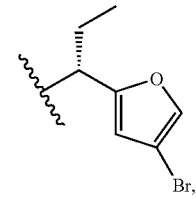
A8.10

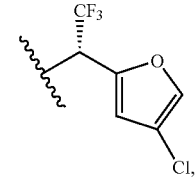
A8.11

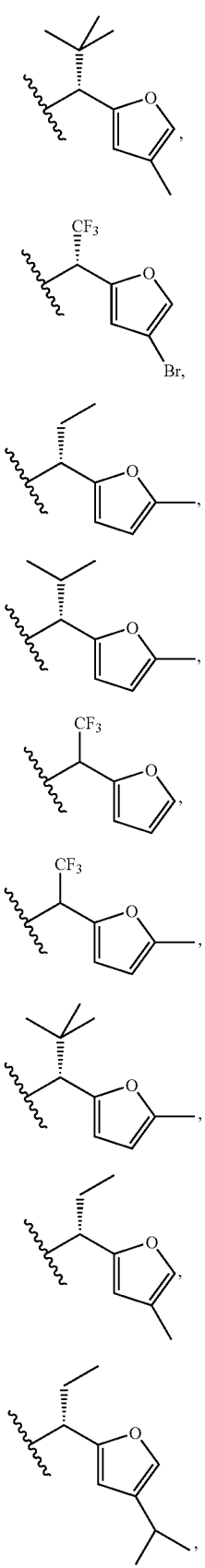
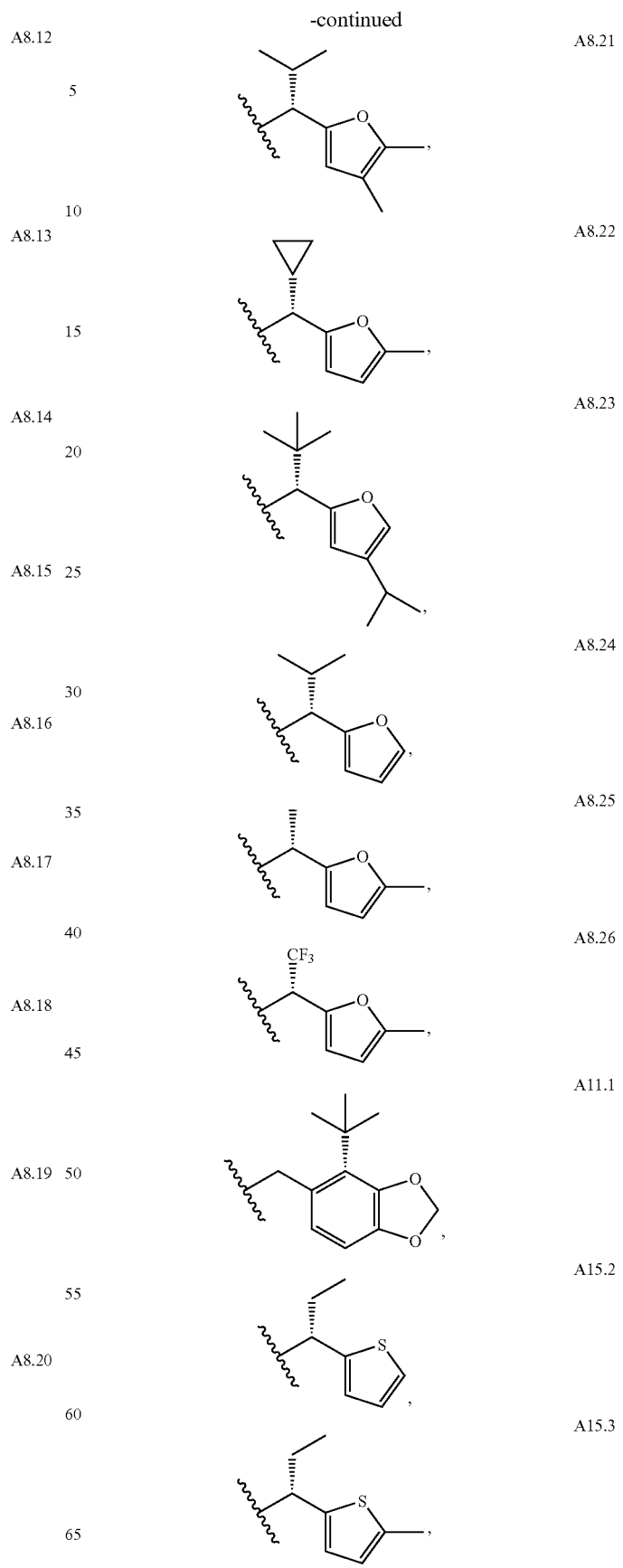

-continued

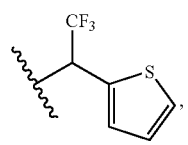
A15.4

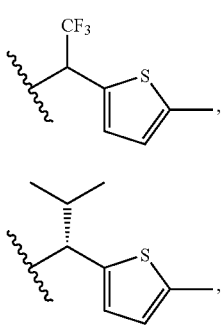
A15.5

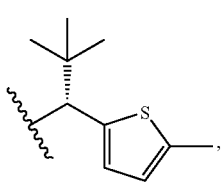
A15.6

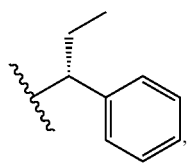
A15.7

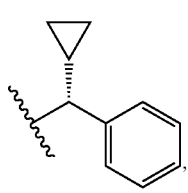
A16.2

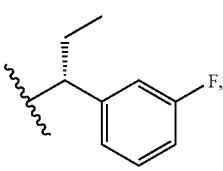
A16.3

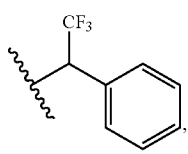
A16.4

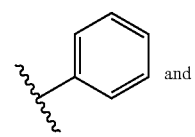
A16.5

A37 and

-continued

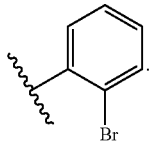
A37.1

Embodiment No. 57 is directed to compounds of formula 1.0 wherein A is selected from the group consisting of: A11.1, A8.12, A8.15, A8.18, A8.21, A8.23, A8.24, A8.25, A8.26, A15.3, A15.7, A16.2, A37 and A37.1, as defined in Embodiment No. 56.

Embodiment No. 58 is directed to compounds of formula 1.0 wherein A is as described in Embodiment No. 56 and B is as described in Embodiment No. 45.

Embodiment No. 59 is directed to compounds of formula 1.0 wherein A is as described in Embodiment No. 50 and B is as described in Embodiment No. 44.

Embodiment No. 60 is directed to compounds of formula 1.0 wherein A is as described in Embodiment No. 49 and B is as described in Embodiment No. 43.

Embodiment No. 61 is directed to compounds of formula 1.0 wherein A is as described in Embodiment No. 47 and B is as described in Embodiment No. 42.

Embodiment No. 62 is directed to compounds of formula 1.0 wherein A is as described in Embodiment No. 46 and B is as described in Embodiment No. 41.

Embodiment No. 63 is directed to compounds of formula 1.0 wherein B is as described in any one of the Embodiment Nos. 1 to 45, and A is as defined in any one of the Embodiment Nos. 46 to 57.

Embodiment No. 64 is directed to compounds of formula 1.0 wherein B is as described in any one of the Embodiment Nos. 1 to 45, and A is an unsubstituted A8 group or a substituted A8 group (as defined for formula 1.0), and all other substituents are as defined for formula 1.0.

Embodiment No. 65 is directed to compounds of formula 1.0 wherein B is described in any one of the Embodiment Nos. 1 to 45, and A is a substituted A8 group, as defined for formula 1.0, and all other substituents are as defined for formula 1.0.

Embodiment No. 66 is directed to compounds of formula 1.0 wherein B is as described in any one of the Embodiment Nos. 1 to 45, and A is an A8 group wherein the furan ring is substituted with at least one (e.g., 1 to 3, or 1 to 2) alkyl group, and all other substituents are as defined for formula 1.0.

Embodiment No. 67 is directed to compounds of formula 1.0 wherein B is as described in any one of the Embodiment Nos. 1 to 45, A is an A8 group wherein the furan ring is substituted with one alkyl group, and all other substituents are as defined for formula 1.0.

Embodiment No. 68 is directed to compounds of formula 1.0 wherein B is as described in any one of the Embodiment Nos. 1 to 45, and A is an A8 group wherein the furan ring is substituted with one $C_1$ to $C_3$ alkyl group (e.g., methyl or isopropyl), and all other substituents are as defined for formula 1.0.

Embodiment No. 69 is directed to compounds of formula 1.0 wherein B is as described in any one of the Embodiment Nos. 1 to 45, and A is as defined in any one of the Embodiment Nos. 64 to 68, except that $R^7$ and $R^8$ are the same or different and each is selected from the group consisting of: H and alkyl.

Embodiment No. 70 is directed to compounds of formula 1.0 wherein B is as described in any one of the Embodiment Nos. 1 to 45, and A is as defined in any one of the Embodiment Nos. 64 to 68, except that $R^7$ is H, and $R^8$ is alkyl (e.g., ethyl or t-butyl).

Embodiment No. 71 is directed to compounds of formula 1.0 wherein:
  substituent A is selected from the group consisting of: A1, A2, A3, A4, A5, A6, A8, A9, A11, A14, A15, A16, A20, A41, A42 and A45, as defined for formula 1.0, and wherein said groups A1, A2, A3, A4, A5, A6, A8, A9, A11, A14, A15, A16 and A20 are unsubstitued or substituted, as defined for formula 1.0, and each $R^7$ and $R^8$ for said A groups is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, —$CO_2R^{13}$, —$CONR^{13}R^{14}$, fluoroalkyl, alkynyl, alkenyl, and cycloalkenyl, and wherein said substituents on said $R^7$ and $R^8$ substituted groups are selected from the group consisting of: a) cyano, b) —$CO_2R^{13}$, c) —$C(O)NR^{13}R^{14}$, d) —$SO_2NR^{13}R^{14}$, e) —$NO_2$, f) —$CF_3$, g) —$OR^{13}$, h) —$NR^{13}R^{14}$, i) —$OC(O)R^{13}$, j) —$OC(O)NR^{13}R^{14}$ halogen, and $R^{8a}$ and $R^9$ for said A groups are as defined in formula 1.0, and
  substituent B in formula 1.0 is selected from the group consisting of: B1.1, B3, B2, B4 and B5, as defined for formula 1.0.

Embodiment No. 72 is directed to compounds of formula 1.0 wherein substituent A is selected from the group consisting of: A1, A2, A3, A4, A5, A6, A8, A9, A11, A14, A15, A16, A20, A41, A42 and A45, as defined for formula 1.0, and wherein:
  said groups A1, A2, A3, A4, A5, A6, A8, A9, A11, A14, A15, A16 and A20 are unsubstitued or substituted with 1 to 3 substituents independently selected from the group consisting of: halogen, alkyl, cycloalkyl, —$CF_3$, cyano, —$OCH_3$, and —$NO_2$, each $R^7$ and $R^8$ for said A1, A2, A3, A4, A5, A6, A8, A9, A11, A14, A15, A16 and A20 is independently selected from the group consisting of: H, alkyl (e.g., methyl, ethyl, t-butyl, and isopropyl), fluoroalkyl (such as, —$CF_3$ and —$CF_2CH_3$), cycloalkyl (e.g., cyclopropyl, and cyclohexyl), and cycloalkylalkyl (e.g., cyclopropylmethyl); and $R^9$ is selected from the group consisting of: H, halogen, alkyl, cycloalkyl, —$CF_3$, cyano, —$OCH_3$, and —$NO_2$, and
  each $R^7$ and $R^8$ for said A41, A42 and A45 groups is independently selected from the group consisting of: H, alkyl (e.g., methyl, ethyl, t-butyl, and isopropyl), fluoroalkyl (such as, —$CF_3$ and —$CF_2CH_3$), cycloalkyl (e.g., cyclopropyl, and cyclohexyl), and cycloalkylalkyl (e.g., cyclopropylmethyl), and $R^{8a}$ for said A41, A42 and A45 groups is as defined in formula 1.0, and $R^9$ for said A41, A42 and A45 groups is selected from the group consisting of: H, halogen, alkyl, cycloalkyl, —$CF_3$, cyano, —$OCH_3$, and —$NO_2$, and
  substituent B is selected from the group consisting of: B1.1, B2, B3, B4 and B5, as defined for formula 1.0, wherein for said B groups:
  $R^2$ is selected from the group consisting of: H, OH, —NHC(O)$R^{13}$ and —$NHSO_2R^{13}$,
  $R^3$ is selected from the group consisting of: —$SO_2NR^{13}R^{14}$, —$NO_2$, cyano, —$C(O)NR^{13}R^{14}$, —$SO_2R^{13}$; and —$C(O)OR^{13}$,
  $R^4$ is selected from the group consisting of: H, —$NO_2$, cyano, —$CH_3$, halogen, and —$CF_3$,
  $R^5$ is selected from the group consisting of: H, —$CF_3$, —$NO_2$, halogen and cyano,
  $R^6$ is selected from the group consisting of: H, alkyl and —$CF_3$,
  each $R^{10}$ and $R^{11}$ is independently selected from the group consisting of:
    $R^{13}$, hydrogen, halogen, —$CF_3$, —$NR^{13}R^{14}$, —$NR^{13}C(O)NR^{13}R^{14}$, —$C(O)OR^{13}$, —SH, —$SO_{(t)}NR^{13}R^{14}$—$SO_2R^{13}$, —$NHC(O)R^{13}$, —$NHSO_2NR^{13}R^{14}$, —$NHSO_2R^{13}$, —$C(O)NR^{13}R^{14}$, —$C(O)NR^{13}OR^{14}$, —$OC(O)R^{13}$, —$COR^{13}$, —$OR^{13}$, and cyano, and
  each $R^{13}$ and $R^{14}$ is independently selected from the group consisting of: H, methyl, ethyl, isopropyl and t-butyl, or $R^{13}$ and $R^{14}$ when taken together with the nitrogen they are attached to in the groups —$C(O)NR^{13}R^{14}$ and —$SO_2NR^{13}R^{14}$ form an unsubstituted or substituted saturated heterocyclic ring (preferably a 3 to 7 membered ring) optionally having one additional heteroatom selected from the group consisting of: O, S or $NR^{18}$; wherein $R^{18}$ is selected from the group consisting of: H, alkyl, aryl, heteroaryl, —$C(O)R^{19}$, —$SO_2R^{19}$ and —$C(O)NR^{19}R^{20}$; wherein each $R^{19}$ and $R^{20}$ is independently selected from the group consisting of: alkyl, aryl and heteroaryl; wherein there are 1 to 3 substituents on the substituted cyclized $R^{13}$ and $R^{14}$ groups (i.e., the substituents on the ring formed when $R^{13}$ and $R^{14}$ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —$C(O)OR^{15}$, —$C(O)NR^{15}R^{16}$, —$SO_tNR^{15}R^{16}$, —$C(O)R^{15}$, —$SO_2R^{15}$ provided that $R^{15}$ is not H, —$NHC(O)NR^{15}R^{16}$ and halogen; and wherein each $R^{15}$ and $R^{16}$ is independently selected from the group consisting: of H, alkyl, aryl, arylalkyl, cycloalkyl and heteroaryl.

Embodiment No. 73 is directed to compounds of formula 1.0 wherein:
  substituent A is selected from the group consisting of A8, A15.1, A16.1, A20.1, A20.2 and A45 (see Embodiment No. 49, for example, for these substitutents),
  said substituents A8, A15.1, A16.1, A20.1, A20.2 are unsubstituted, or are substituted with 1 to 3 substituents independently selected from the group consisting of: H, F, Cl, Br, alkyl, cycloalkyl, and —$CF_3$, $R^7$ for said substituents A8, A15.1, A16.1, A20.1, A20.2 is selected from the group consisting of: H, —$CF_3$, —$CF_2CH_3$, methyl, ethyl, isopropyl, cyclopropyl and t-butyl; and $R^8$ for said substituents A8, A15.1, A16.1, A20.1, A20.2 is H,
  $R^7$ for said substitutent A45 is selected from the group consisting of: H, —$CF_3$, —$CF_2CH_3$, methyl, ethyl, isopropyl, cyclopropyl and t-butyl, and $R^8$ for said substitutent A45 is H, and $R^{8a}$ for said substitutent A45 is as defined for formula 1.0,
  substituent B is selected from the group consisting of B1.1 (see Embodiment No. 4 for example) and B3 (see Embodiment No. 43 for example), wherein:
  $R^2$ is selected from the group consisting of: H, OH, —NHC(O)$R^{13}$ and —$NHSO_2R^{13}$,
  $R^3$ is selected from the group consisting of: —$C(O)NR^{13}R^{14}$, —$SO_2NR^{13}R^{14}$, —$NO_2$, cyano, —$SO_2R^{13}$; and —$C(O)OR^{13}$,
  $R^4$ is selected from the group consisting of: H, —$NO_2$, cyano, —$CH_3$ or —$CF_3$, $R^5$ is selected from the group consisting of: H, —$CF_3$, —$NO_2$, halogen and cyano, $R^6$ is selected from the group consisting of: H, alkyl and —$CF_3$, $R^{11}$ is selected from the group consisting of: H, halogen and alkyl, and each $R^{13}$ and $R^{14}$ is independently selected from the group consisting of: H, methyl, ethyl, isopropyl and t-butyl, or $R^{13}$ and $R^{14}$ when taken together with the nitrogen they are attached to in the groups —$C(O)NR^{13}R^{14}$ and —$SO_2NR^{13}R^{14}$ form an unsubstituted or substituted saturated heterocyclic ring (preferably a 3 to 7 membered ring) optionally having one additional heteroatom selected from O, S or $NR^{18}$ wherein $R^{18}$ is selected from H, alkyl, aryl, heteroaryl, —$C(O)R^{19}$, —$SO_2R^{19}$ and —$C(O)NR^{19}R^{20}$, wherein each $R^{19}$ and $R^{20}$ is independently selected from alkyl, aryl and heteroaryl, wherein there are 1 to 3 substituents on the substituted cyclized $R^{13}$ and $R^{14}$ groups (i.e., on the ring formed when $R^{13}$ and $R^{14}$ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —$C(O)OR^{15}$, —$C(O)NR^{15}R^{16}$— $SO_tNR^{15}R^{16}$, —$C(O)R^{15}$, —$SO_2R^{15}$ provided that $R^{15}$ is not H, —$NHC(O)NR^{15}R^{16}$ and halogen; and wherein each $R^{15}$ and $R^{16}$ is independently selected from the group consisting of: H, alkyl, aryl, arylalkyl, cycloalkyl and heteroaryl.

Embodiment No. 74 is directed to compounds of formula 1.0 wherein substituent A is selected from the group consisting of A8, A15.1, A16.1, A20.1, A20.2 and A45, as previously defined, wherein:

said A8, A15.1, A16.1, A20.1 and A20.2 substituents are unsubstituted, or substituted with 1 to 3 substituents independently selected from the group consisting of: F, Cl, Br, alkyl, cycloalkyl, and —$CF_3$, $R^7$ for said A8, A5.1, A16.1, A20.1 and A20.2 substituents is selected from the group consisting of: H, —$CF_3$, —$CF_2CH_3$, methyl, ethyl, isopropyl, cyclopropyl and t-butyl; and $R^8$ for said A8, A15.1, A16.1, A20.1 and A20.2 substituents is H, said $R^7$ for said A45 substituent is selected from the group consisting of: H, —$CF_3$, —$CF_2CH_3$, methyl, ethyl, isopropyl, cyclopropyl and t-butyl, and $R^8$ is H; and $R^{8a}$ is as defined for formula 1.0;

substituent B is selected from the group consisting of B1.1 and B3, as previously defined, wherein $R^2$ is selected from the group consisting of: H, OH, —NHC(O)$R^{13}$ and —$NHSO_2R^{13}$, $R^3$ is selected from the group consisting of: —$C(O)NR^{13}R^{14}$—$SO_2NR^{13}R^{14}$, —$NO_2$, cyano, and —$SO_2R^{13}$, $R^4$ is selected from the group consisting of: H, —$NO_2$, cyano, —$CH_3$ or —$CF_3$, $R^5$ is selected from the group consisting of: H, —$CF_3$, —$NO_2$, halogen and cyano, $R^6$ is selected from the group consisting of: H, alkyl and —$CF_3$, $R^{11}$ is selected from the group consisting of: H, halogen and alkyl, and each $R^{13}$ and $R^{14}$ is independently selected from the group consisting of: methyl and ethyl.

Embodiment No. 75 is directed to compounds of formula 1.0 wherein substituent A is as defined in Embodiment No. 56, and substitutent B is selected from the group consisting of B1.1 and B3, as previously defined, wherein: $R^2$ is —OH, $R^3$ is selected from the group consisting of: —$SO_2NR^{13}R^{14}$ and —$CONR^{13}R^{14}$, $R^4$ is selected form the group consisting of: H, —$CH_3$ and —$CF_3$, $R^5$ is selected from the group consisting of: H and cyano, $R^6$ is selected from the group consisting of: H, —$CH_3$ and —$CF_3$, $R^{11}$ is H, and $R^{13}$ and $R^{14}$ are methyl.

Embodiment No. 76 is directed to compounds of formula 1.0 wherein substituent A is as defined in Embodiment No. 71, and substituent B is B3, as defined for formula 1.0.

Embodiment No. 77 is directed to compounds of formula 1.0 wherein substituent A is as defined in Embodiment No. 71 and substituent B is B3, as defined in formula 1.0, wherein:

$R^2$ is selected from the group consisting of: H, OH, —NHC(O)$R^{13}$ and —$NHSO_2R^{13}$, $R^3$ is selected from the group consisting of: —$SO_2NR^{13}R^{14}$, —$NO_2$, cyano, —$C(O)NR^{13}R^{14}$, —$SO_2R^{13}$, and —$C(O)OR^{13}$, $R^{11}$ is selected from the group consisting of: $R^{13}$, hydrogen, halogen, —$CF_3$, —$NR^{13}R^{14}$, —$NR^{13}C(O)NR^{13}R^{14}$, —$C(O)OR^{13}$, —SH, —$SO_{(t)}NR^{13}R^{14}$—$SO_2R^{13}$, —$NHC(O)R^{13}$, —$NHSO_2NR^{13}R^{14}$, —$NHSO_2R^{13}$, —$C(O)NR^{13}R^{14}$, —$C(O)NR^{13}OR^{14}$, —$OC(O)R^{13}$, —$COR^{13}$, —$OR^{13}$, and cyano, each $R^{13}$ and $R^{14}$ is independently selected from the group consisting of: H, methyl, ethyl, isopropyl and t-butyl, or $R^{13}$ and $R^{14}$ when taken together with the nitrogen they are attached to in the groups —$C(O)NR^{13}R^{14}$ and —$SO_2NR^{13}R^{14}$, form an unsubstituted or substituted saturated heterocyclic ring (preferably a 3 to 7 membered ring) optionally having one additional heteroatom selected from the group consisting of: O, S or $NR^{18}$; wherein $R^{18}$ is selected from the group consisting of: 1H, alkyl, aryl, heteroaryl, —$C(O)R^{19}$, —$SO_2R^{19}$ and —$C(O)NR^{19}R^{20}$, wherein each $R^{19}$ and $R^{20}$ is independently selected from the group consisting of: alkyl, aryl and heteroaryl, wherein there are 1 to 3 substituents on the substituted cyclized $R^{13}$ and $R^{14}$ groups (i.e., the substituents on the ring formed when $R^{13}$ and $R^{14}$ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —$C(O)OR^{15}$, —$C(O)NR^{15}R^{15}R^{16}$, —$SO_tNR^{15}R^{16}$, —$C(O)R^{15}$, —$SO_2R^{15}$ provided that $R^{15}$ is not H, —$NHC(O)NR^{15}R^{16}$ and halogen, and wherein each $R^{15}$ and $R^{16}$ is independently selected from the group consisting: of H, alkyl, aryl, arylalkyl, cycloalkyl and heteroaryl.

Embodiment No. 78 is directed to compounds of formula 1.0 wherein A is as defined in Embodiment No. 72, and B is B3, as defined in formula 1.0, wherein:

$R^2$ is selected from the group consisting of: H, OH, —NHC(O)$R^{13}$ or and —$NHSO_2R^{13}$, $R^3$ is —$SO_2NR^{13}R^{14}$, $R^{11}$ is selected from the group consisting of: $R^{13}$, hydrogen, halogen, —$CF_3$, —$NR^{13}R^{14}$, —$NR^{13}C(O)NR^{13}R^{14}$, —$C(O)OR^{13}$, —SH, —$SO_{(t)}NR^{13}R^{14}$, —$SO_2R^{13}$, —$NHC(O)R^{13}$, —$NHSO_2NR^{13}R^{14}$, —$NHSO_2R^{13}$, —$C(O)NR^{13}R^{14}$, —$C(O)NR^{13}OR^{14}$, —$OC(O)R^{13}$, —$COR^{13}$, —$OR^{13}$, and cyano, each $R^{13}$ and $R^{14}$ is independently selected from the group consisting of: H, methyl, ethyl, isopropyl and t-butyl, or $R^{13}$ and $R^{14}$ when taken together with the nitrogen they are attached to in the group —$SO_2NR^{13}R^{14}$ form an unsubstituted or substituted saturated heterocyclic ring (preferably a 3 to 7 membered ring) optionally having one additional heteroatom is selected from the group consisting of: O, S or $NR^{18}$, wherein $R^{18}$ is selected from the group consisting of: H, alkyl, aryl, heteroaryl, —C(O)$R^{19}$, —SO$_2R^{19}$ and —C(O)$NR^{19}R^{20}$, wherein each $R^{19}$ and $R^{20}$ is independently selected from the group consisting of: alkyl, aryl and heteroaryl, wherein there are 1 to 3 substituents on the substituted cyclized $R^{13}$ and $R^{14}$ groups (i.e., the substituents on the ring formed when $R^{13}$ and $R^{14}$ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)$OR^{15}$, —C(O)$NR^{15}R^{16}$, —SO$_t$NR$^{15}R^{16}$, —C(O)$R^{15}$, —SO$_2R^{15}$ provided that $R^{15}$ is not H, —NHC(O)$NR^{15}R^{16}$ and halogen; and wherein each $R^{15}$ and $R^{16}$ is independently selected from the group consisting: of H, alkyl, aryl, arylalkyl, cycloalkyl and heteroaryl.

Embodiment No. 79 is directed to compounds of formula 1.0 wherein substitutent A is as defined in Embodiment No. 73 and substituent B is B3, as defined in formula 1.0, wherein:
$R^2$ is selected from the group consisting of: H, OH, —NHC(O)$R^{13}$ and —NHSO$_2R^{13}$,
$R^3$ is selected from the group consisting of: —C(O)$NR^{13}R^{14}$, —SO$_2NR^{13}R^{14}$, —NO$_2$, cyano, —SO$_2R^{13}$; and —C(O)$OR^{13}$,
$R^{11}$ is selected from the group consisting of: H, halogen and alkyl, and
each $R^{13}$ and $R^{14}$ is independently selected from the group consisting of: H, methyl, ethyl, isopropyl and t-butyl.

Embodiment No. 80 is directed to compounds of formula 1.0 wherein substituent A is as defined in Embodiment No. 73, and substituent B is B3, as defiend in formula 1.0, wherein:
$R^2$ is selected from the group consisting of: H, OH, —NHC(O)$R^{13}$ and —NHSO$_2R^{13}$ (preferably —OH),
$R^3$ is —SO$_2NR^{13}R^{14}$,
$R^{11}$ is selected from the group consisting of: H, halogen and alkyl (preferably H), and
each $R^{13}$ and $R^{14}$ is independently selected from the group consisting of: H and ethyl, preferably $R^{13}$ and $R^{14}$ are ethyl.

Embodiment No. 81 is directed to compounds of formula 1.0 wherein substitutent A is as defined in Embodiment No. 75 and substituent B is B3, as defined in formula 1.0, wherein $R^2$ is —OH, $R^3$ is —SO$_2NR^{13}R^{14}$, $R^{11}$ is H, and $R^{13}$ and $R^{14}$ are ethyl.

Embodiment No. 82 is directed to compounds of formula 1.0 wherein B is selected from the group consisting of: B1 as defined in Embodiment No. 3, B2, B3, B4, B5, B6, B7, B8, B9, B10, B11, B12 and B13, and all other substituents are as defined for formula 1.0.

Embodiment No. 83 is directed to compounds of formula 1.0 wherein B is selected from the group consisting of: B9, B10, B11, B12 and B13, as defined for formula 1.0, and all other substituents are as defined for formula 1.0.

Embodiment No. 84 is directed to compounds of formula 1.0 wherein B is B9, as defined for formula 1.0, and all other substituents are as defined for formula 1.0.

Embodiment No. 85 is directed to compounds of formula 1.0 wherein B is B10, as defined for formula 1.0, and all other substituents are as defined for formula 1.0.

Embodiment No. 86 is directed to compounds of formula 1.0 wherein B is B11, as defined for formula 1.0, and all other substituents are as defined for formula 1.0.

Embodiment No. 87 is directed to compounds of formula 1.0 wherein B is B12, as defined for formula 1.0, and all other substituents are as defined for formula 1.0.

Embodiment No. 88 is directed to compounds of formula 1.0 wherein B is B13, as defined for formula 1.0, and all other substituents are as defined for formula 1.0.

Embodiment No. 89 is directed to compounds of formula 1.0 wherein B is B14, as defined for formula 1.0, and all other substituents are as defined for formula 1.0.

Embodiment No. 90 is directed to compounds of formula 1.0 wherein B is B15, as defined for formula 1.0, and all other substituents are as defined for formula 1.0.

Embodiment No. 91 is directed to compounds of formula 1.0 wherein B is B16, as defined for formula 1.0, and all other substituents are as defined for formula 1.0.

Embodiment No. 92 is directed to compounds of formula 1.0 wherein B is B17, as defined for formula 1.0, and all other substituents are as defined for formula 1.0.

Embodiment No. 93 is directed to compounds of formula 1.0 wherein B is B18, as defined for formula 1.0, and all other substituents are as defined for formula 1.0.

Embodiment No. 94 is directed to compounds of formula 1.0 B is described in any of Embodiment Nos. 82 to 93 and A is as described in any of Embodiments Nos. 58-70.

Embodiment No. 95 is directed to compounds of formula 1.0 wherein X is O.

Embodiment No. 96 is directed to compounds of formula 1.0 wherein X is S.

Embodiment No. 97 is directed to the compounds of any one of Embodiment Nos. 1-94 wherein X is O.

Embodiment No. 98 is directed to the compounds of any one of Embodiment Nos. 1-94 wherein X is S.

Embodiment No. 99 is directed to any one of the Embodiment Nos. 1 to 98 wherein the compound of formula 1.0 is a pharmaceutically acceptable salt.

Embodiment No. 100 is directed to any one of the Embodiment Nos. 1 to 98 wherein the compound of formula 1.0 is a sodium salt.

Embodiment No. 101 is directed to any one of the Embodiment Nos. 1 to 98 wherein the compound of formula 1.0 is a calcium salt.

Embodiment No. 102 is directed to a compound selected from the group consisting of the final compounds of Examples 1, 2a, 2b, 3a, 3b, 4a, 4b, 5a, 5b, 6a, 6b, 7a, 7b, 8a, 8b, 9a, 9b, 10a, 10b, 11a, 11b, 12a, 12b, 13a, 13b, 14a, 14b, 15a, 15b, 16a, 16b, 17a, 17b, 18a, 18b, 19a, 19b, 20a, 20b, 21a, 21b, 22a, 22b, 23a, 23b, 24a, 24b, 25a, 25b, 26a, 26b, 27a, 27b, 28a, 28b, 29a, 29b, 30a, 30b, 31a, 31b, 32a, 32b, 33a, 33b, 34a, 34b, 35a, 35b, 36a, 36b, 37a, 37b, 38a, 38b, 39a, 39b, 40a, 40b, 41a, 41b, 42a, 42b, 43a, 43b, 44a, 44b, 45a, 46a, 46b, 47a, 47b, 48a, 48b, 49a, 49b, 50a, 50b, 51a, 51b, 52a, and 52b.

Embodiment No. 103 is directed to a compound selected from the group consisting of the final compounds of Examples 1, 2a, 3a, 4a, 5a, 6a, 7a, 8a, 9a, 10a, 11a, 12a, 13a, 14a, 15a, 16a, 17a, 18a, 19a, 20a, 21a, 22a, 23a, 24a, 25a, 27a, 28a, 29a, 30a, 31a, 32a, 33a, 34a, 35a, 36a, 37a, 38a, 39a, 40a, 41a, 42a, 43a, 44a, 45a, 47a, 48a, 49a, 50a, 51a, and 52a.

Embodiment No. 104 is directed to a compound selected from the group consisting of the final compounds of Examples 2b, 3b, 4b, 5b, 6b, 7b, 8b, 9b, 10b, 11b, 12b, 13b, 14b, 15b, 16b, 17b, 18b, 19b, 20b, 21b, 22b, 23b, 24b, 26b, 27b, 28b, 29b, 30b, 31b, 32b, 33b, 34b, 35b, 36b, 37b, 38b, 39b, 40b, 41b, 42b, 43b, 44b, 46b, 47b, 48b, 49b, 50b, 51 b, and 52b.

Embodiment No. 105 is directed to a compound selected from the group consisting of the final compounds of Examples: 2a, 2b, 3a, 3b, 5a, 5b, 7a, 7b, 8a, 8b, 9a, 9b, 10a, 10b, 14a, 14b, 15a, 15b, 16a, 16b, 17a, 17b, 18a, 18b, 19a, 19b, 21a, 21b, 22a, 22b, 24a, 24b, 25a, 25b, 26a, 26b, 27a, 27b, 28a, 28b, 29a, 29b, 30a, 30b, 31a, 31b, 32a, 32b, 35a, 35b, 37a, 37b, 39a, 39b, 40a, 40b, 41a, 41b, 42a, 42b, 44a, 44b, 45a, 45b, 46a, 46b, 48a, 48b, 50a, and 50b.

Embodiment No. 106 is directed to a compound selected from the group consisting of the final compounds of Examples: 3a, 3b, 5a, 5b, 8a, 8b, 10a, 10b, 14a, 14b, 16a, 16b, 17a, 17b, 18a, 18b, 19a, 19b, 26a, 26b, 28a, 28b, 30a, 30b, 31a, 31b, 37a, 37b, 40a, 40b, 41a, 41 b, 42a, 42b, 44a, 44b, 45a, 45b, 46a, 46b, 48a, and 48b.

Embodiment No. 107 is directed to a compound selected from the group consisting of the final compounds of Examples: 3a, 3b, 5a, 5b, 8a, 8b, 10a, 10b, 14a, 14b, 17a, 17b, 18a, 18b, 22a, 22b, 28a, 28b, 29a, 29b, 32a, 32b, 40a, 40b, 41a, 41b, 45a, and 45b.

Embodiment No. 108 is directed to the final compound of Example 1.

Embodiment No. 109 is directed to any one of the Embodiment Nos. 102 to 108 wherein the compound is a pharmaceutically acceptable salt.

Embodiment No. 110 is directed to any one of the Embodiment Nos. 102 to 108 wherein the compound is a sodium salt.

Embodiment No. 111 is directed to any one of the Embodiment Nos. 102 to 108 wherein the compound is a calcium salt.

Embodiment No. 112 is directed to a pharmaceutical composition comprising at least one (e.g., 1 to 3, usually 1) compound of formula 1.0 and a pharmaceutically acceptable carrier (or diluent).

Embodiment No. 113 is directed to a pharmaceutical composition comprising at least one (e.g., 1 to 3, usually 1) compound of formula 1.0 in combination with another pharmaceutical (e.g., another active ingredient, another drug, or another medicament).

Embodiment No. 114 is directed to a pharmaceutical composition comprising at least one (e.g., 1 to 3, usually 1) compound of formula 1.0 and a pharmaceutically acceptable carrier (or diluent) in combination with another pharmaceutical (e.g., another active ingredient, another drug, or another medicament).

Embodiment No. 115 is directed to a pharmaceutical composition comprising at least one (e.g., 1 to 3, usually 1) compound of any one of Embodiment Nos. 1 to 111 and a pharmaceutically acceptable carrier (or diluent).

Embodiment No. 116 is directed to a pharmaceutical composition comprising at least one (e.g., 1 to 3, usually 1) compound of any one of Embodiment Nos. 1 to 111 in combination with another pharmaceutical (e.g., another active ingredient, another drug, or another medicament).

Embodiment No. 117 is directed to a pharmaceutical composition comprising at least one (e.g., 1 to 3, usually 1) compound of any one of Embodiment Nos. 1 to 111 and a pharmaceutically acceptable carrier (or diluent) in combination with another pharmaceutical (e.g., another active ingredient, another drug, or another medicament).

The compounds of formula 1.0 (e.g., the compounds of Embodiment Nos. 1 to 111) are useful for treating a chemokine mediated disease (or condition), wherein the chemokine binds to a CXCR2 and/or CXCR1 receptor, in a patient in need of such treatment.

Therefore, this invention is also directed to a method of treating a chemokine mediated disease (or condition), wherein the chemokine binds to a CXCR2 and/or CXCR1 receptor, in a patient (e.g., a mammal, preferably a human being) in need of such treatment comprising administering to said patient a therapeutically effective amount of at least one (e.g., 1-3, and usually one) compound of formula 1.0, or a pharmaceutically acceptable salt thereof.

Examples of chemokine mediated diseases or conditions include: acute inflammation, chronic inflammation, rheumatoid arthritis, pain (such as, for example acute inflammatory pain, chronic inflammatory pain, acute neuropathic pain, and chronic neuropathic pain), psoriasis, atopic dermatitis, asthma, COPD, cancer, adult respiratory disease, arthritis, inflammatory bowel disease, Crohn's disease, ulcerative colitis, septic shock, endotoxic shock, gram negative sepsis, toxic shock syndrome, stroke, cardiac and renal reperfusion injury, glomerulonephritis, thrombosis, Alzheimer's disease, graft vs. host reaction, allograft rejections, malaria, acute respiratory distress syndrome, delayed type hypersensitivity reaction, atherosclerosis, cerebral and cardiac ischemia, osteoarthritis, multiple sclerosis, restinosis, angiogenesis, osteoporosis, gingivitis, respiratory viruses, herpes viruses, hepatitis viruses, HIV, Kaposi's sarcoma associated virus, meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute and chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred and corneal neovascularization, polymyositis, vasculitis, acne, gastric and duodenal ulcers, celiac disease, esophagitis, glossitis, airflow obstruction, airway hyperresponsiveness, bronchiectasis, bronchiolitis, bronchiolitis obliterans, chronic bronchitis, cor pulmonae, cough, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy, periodontitis, transplant reperfusion injury and early transplantation rejection.

One embodiment of the present invention is directed to a method of treating cancer in a patient (e.g., a mammal, such as a human being) in need of such treatment, comprising administering to said patient a therapeutically effective amount of at least one (e.g., 1-3, and usually one) compound of formula 1.0, or a pharmaceutically acceptable salt thereof.

Another embodiment of the present invention is directed to a method of treating cancer in a patient (e.g., a mammal, such as a human being) in need of such treatment, comprising administering to said patient, concurrently or sequentially, a therapeutically effective amount of (a) at least one (e.g., 1-3, and usually one) compound of formula 1.0, or a pharmaceutically acceptable salt thereof, and (b) a microtubule affecting agent or an antineoplastic agent or an anti-angiogenesis agent or a VEGF receptor kinase inhibitor or antibodies against the VEGF receptor or interferon, and/or c) radiation.

In another embodiment of this invention directed to the treatment of cancer, at least one (e.g., 1-3, and usually one) compound of formula 1.0, or a pharmaceutically acceptable salt thereof, is administered in combination with antineoplastic agents (e.g., one or more, such as one, or such as one or two), selected from the group consisting of: gemcitabine, paclitaxel (Taxol®), 5-Fluorouracil (5-FU), cyclophosphamide (Cytoxan®), temozolomide, taxotere and Vincristine.

Another embodiment of the invention is directed to a method treating cancer, comprising administering to a patient in need thereof, concurrently or sequentially, a therapeutically effective amount of (a) at least one (e.g., 1-3, and usually one) compound of formula 1.0, or a pharmaceutically acceptable salt thereof, and (b) an antineoplastic agent, microtubule affecting agent or anti-angiogenesis agent.

Another embodiment of the present invention is directed to a method of treating cancer in a patient (e.g., a mammal, such as a human being) in need of such treatment, comprising administering, concurrently or sequentially, an effective amount of (a) a compound of formula 1.0, or a pharmaceutically acceptable salt thereof, and (b) a microtubule affecting agent (e.g., paclitaxel).

Another embodiment of the present invention is directed to a method of treating cancer in a patient (e.g., a mammal, such as a human being) in need of such treatment, wherein said cancer is selected from the group consisting of: melanoma, gastric carcinoma, and non-small cell lung carcinoma, comprising administering to said patient a therapeutically effective amount of at least one (e.g., 1-3, and usually one) compound of formula 1.0, or a pharmaceutically acceptable salt thereof.

Another embodiment of this invention is directed to a method of treating cancer in a patient (e.g., a mammal, such as a human being) in need of such treatment, wherein said cancer is selected from the group consisting of: melanoma, gastric carcinoma, and non-small cell lung carcinoma, comprising administering to said patient an effective amount of at least one (e.g., 1-3, and usually one) compound of formula 1.0, or a pharmaceutically acceptable salt thereof, in combination with the administration of at least one anticancer agent.

Another embodiment of this invention is directed to a method of treating cancer in a patient (e.g., a mammal, such as a human being) in need of such treatment, wherein said cancer is selected from the group consisting of: melanoma, gastric carcinoma, and non-small cell lung carcinoma, comprising administering to said patient an effective amount of at least one (e.g., 1-3, and usually one) compound of formula 1.0, or a pharmaceutically acceptable salt thereof, in combination with the administration of at least one anticancer agent said anticancer agent is selected from the group consisting of: alkylating agents, antimetabolites, natural products and their derivatives, hormones, anti-hormones, anti-angiogenic agents and steroids, and synthetics.

Another embodiment of the present invention is directed to a method of treating cancer in a patient (e.g., a mammal, such as a human being) in need of such treatment comprising administering to said patient a therapeutically effective amount of at least one (e.g., 1-3, and usually one) compound of formula 1.0, or a pharmaceutically acceptable salt thereof.

Another embodiment of this invention is directed to a method of treating cancer in a patient (e.g., a mammal, such as a human being) in need of such treatment comprising administering to said patient an effective amount of at least one (e.g., 1-3, and usually one) compound of formula 1.0, or a pharmaceutically acceptable salt thereof, in combination with the administration of at least one anticancer agent.

Another embodiment of this invention is directed to a method of treating cancer in a patient (e.g., a mammal, such as a human being) in need of such treatment comprising administering to said patient an effective amount of at least one (e.g., 1-3, and usually one) compound of formula 1.0, or a pharmaceutically acceptable salt thereof, in combination with the administration of at least one anticancer agent said anticancer agent is selected from the group consisting of: alkylating agents, antimetabolites, natural products and their derivatives, hormones, anti-hormones, anti-angiogenic agents and steroids, and synthetics.

Another embodiment of this invention is directed to a method of inhibiting angiogenesis, in a patient in need of such treatment, comprising administering to said patient an effective amount of at least one compound of formula 1.0, or a pharmaceutically acceptable salt thereof.

Another embodiment of this invention is directed to a method of treating angiogenic ocular disease (e.g., ocular inflammation, retinopathy of prematurity, diabetic retinopathy, macular degeneration with the wet type preferred and corneal neovascularization) in a patient in need of such treatment, comprising administering to said patient an effective amount of at least one compound of formula 1.0, or a pharmaceutically acceptable salt thereof.

Another embodiment of this invention is directed to a method of treating a disease selected from the group consisting of: gingivitis, respiratory viruses, herpes viruses, hepatitis viruses, HIV, kaposi's sarcoma associated virus and atherosclerosis, in a patient in need of such treatment, comprising administering to said patient an effective amount of at least one compound of formula 1.0, or a pharmaceutically acceptable salt thereof.

Another embodiment of the present invention is directed to a method of treating pain, in a patient in need of such treatment (e.g., a mammal, preferably a human being) comprising administering to said patient a therapeutically effective amount of at least one (e.g., 1-3, and usually one) compound of formula 1.0, or a pharmaceutically acceptable salt thereof.

Another embodiment of this invention is directed to a method of treating pain in a patient in need of such treatment comprising administering to said patient a therapeutically effective amount of at least one (e.g., 1, 2 or 3, and usually one) compound of formula 1.0, or a pharmaceutically acceptable salt thereof, concurrently or sequentially with a therapeutically effective amount of at least one medicament (e.g., 1, 2 or 3, and usually one) selected from the group consisting of: NSAIDs, COXIB inhibitors, anti-depressants, anti-convulsants, anti-TNFα antibodies and TNFα antagonists.

Another embodiment of the present invention is directed to a method of treating acute inflammatory pain, in a patient in need of such treatment (e.g., a mammal, preferably a human being) comprising administering to said patient a therapeutically effective amount of at least one (e.g., 1-3, and usually one) compound of formula 1.0, or a pharmaceutically acceptable salt thereof.

Another embodiment of the present invention is directed to a method of treating chronic inflammatory pain, in a patient in need of such treatment (e.g., a mammal, preferably a human being) comprising administering to said patient a therapeutically effective amount of at least one (e.g., 1-3, and usually one) compound of formula 1.0, or a pharmaceutically acceptable salt thereof.

Another embodiment of the present invention is directed to a method of treating acute neuropathic pain, in a patient in need of such treatment (e.g., a mammal, preferably a human being) comprising administering to said patient a therapeutically effective amount of at least one (e.g., 1-3, and usually one) compound of formula 1.0, or a pharmaceutically acceptable salt thereof.

Another embodiment of the present invention is directed to a method of treating chronic neuropathic pain, in a patient in need of such treatment (e.g., a mammal, preferably a human being) comprising administering to said patient a therapeutically effective amount of at least one (e.g., 1-3, and usually one) compound of formula 1.0, or a pharmaceutically acceptable salt thereof.

Another embodiment of the present invention is directed to a method of treating COPD, in a patient in need of such treatment (e.g., a mammal, preferably a human being) comprising administering to said patient a therapeutically effective amount of at least one (e.g., 1-3, and usually one) compound of formula 1.0, or a pharmaceutically acceptable salt thereof.

Another embodiment of the present invention is directed to a method of treating acute inflammation, in a patient in need of such treatment (e.g., a mammal, preferably a human being) comprising administering to said patient a therapeutically effective amount of at least one (e.g., 1-3, and usually one) compound of formula 1.0, or a pharmaceutically acceptable salt thereof.

Another embodiment of the present invention is directed to a method of treating chronic inflammation, in a patient in need of such treatment (e.g., a mammal, preferably a human being) comprising administering to said patient a therapeutically effective amount of at least one (e.g., 1-3, and usually one) compound of formula 1.0, or a pharmaceutically acceptable salt thereof.

Another embodiment of the present invention is directed to a method of treating rheumatoid arthritis, in a patient in need of such treatment (e.g., a mammal, preferably a human being) comprising administering to said patient a therapeutically effective amount of at least one (e.g., 1-3, and usually one) compound of formula 1.0, or a pharmaceutically acceptable salt thereof.

Another embodiment of the present invention is directed to a method of treating arthritis, in a patient in need of such treatment (e.g., a mammal, preferably a human being) comprising administering to said patient a therapeutically effective amount of at least one (e.g., 1-3, and usually one) compound of formula 1.0, or a pharmaceutically acceptable salt thereof.

Another embodiment of this invention is directed to a pharmaceutical composition comprising at least one (e.g., 1-3, usually 1) compound of formula 1.0, or a pharmaceutically acceptable salt thereof, and a pharmaceutically acceptable carrier.

Another embodiment of this invention is directed to a pharmaceutical composition comprising at least one (e.g., 1-3, usually 1) compound of formula 1.0, or a pharmaceutically acceptable salt thereof, in combination with at least one (e.g., 1-3, usually 1) other pharmaceutical (i.e., a drug or medicament).

Examples of pain include, but are not limited to, the pain associated with: allodynia, ankylosing spondylitis, appendicitis, autoimmune disorders, bacterial infections, Behcet's syndrome, broken bones, bronchitis, burns, bursitis, cancer including metastatic cancer, candidiasis, cardiovascular conditions, casualgia, chemical injury, childbirth (e.g., labor), chronic regional neuropathies, Crohn's disease, colorectal cancer, connective tissue injuries, conjunctivitis, COPD, decreased intracranial pressure, dental procedures, dermatitis, diabetes, diabetic neuropathy, dysesthesia, dysmenorrhea, eczema, emphysema, fever, fibromyalgia, gastric ulcer, gastritis, giant cell arteritis, gingivitis, gout, gouty arthritis, headache, headache pain resulting from lumbar puncture, headaches including migraine headache, herpes simplex virus infections, HIV, Hodgkin's disease, hyperalgesia, hypersensitivity, inflammatory bowel disease, increased intracranial pressure, irritable bowel syndrome, ischemia, juvenile arthritis, kidney stones, lumbar spondylanhrosis, lower back, upper back and lumbrosacral conditions, lumbar spondylarthrosis, menstrual cramps, migraines, minor injuries, multiple sclerosis, myasthenia gravis, myocarditis, muscle strains, musculoskeletal conditions, myocardial ischemia, nephritic syndrome, nerve root avulsion, neuritis, nutritional deficiency, ocular and corneal conditions, ocular photophobia, ophthalmic diseases, osteoarthritis, otic surgery, otitis externa, otitis media, periarteritis nodosa, peripheral neuropathies, phantom limb pain, polymyositis, post-herpetic neuralgia, post-operative/surgical recovery, post-thoracotomy, psoriatic arthritis, pulmonary fibrosis, pulmonary edema, radiculopathy, reactive arthritis, reflex sympathetic dystrophy, retinitis, retinopathies, rheumatic fever, rheumatoid arthritis, sarcoidosis, sciatica, scleroderma, sickle cell anemia, sinus headaches, sinusitis, spinal cord injury, spondyloarthropathies, sprains, stroke, swimmer's ear, tendonitis, tension headaches, thalamic syndrome, thrombosis, thyroiditis, toxins, traumatic injury, trigeminal neuralgia, ulcerative colitis, urogenital conditions, uveitis, vaginitis, vascular diseases, vasculitis, viral infections and/or wound healing. This embodiment includes the treatment of acute pain but does not include the treatment of acute inflammatory pain, chronic inflammatory pain, acute neuropathic pain and chronic neuropathic pain.

NSAIDs are well known to those skilled in the art and can be used in their known dosages and dosage regimens. Examples of NSAIDs include but are not limited to: piroxicam, ketoprofen, naproxen, indomethacin, and ibuprofen COXIB inhibitors are well known to those skilled in the art and can be used in their known dosages and dosage regimens. Examples of COXIB inhibitors include but are not limited to: rofecoxib, celecoxib, etoricoxib, valdecoxib and melotican.

Anti-depressants are well known to those skilled in the art and can be used in their known dosages and dosage regimens. Examples of anti-depressants include but are not limited to: amitriptyline and nortriptyline Anti-convulsants are well known to those skilled in the art and can be used in their known dosages and dosage regimens. Examples of Anti-convulsants include but are not limited to: gabapentin, carbamazepine, pregabalin, and lamotrigine.

Anti-TNFα antibodies are well known to those skilled in the art and can be used in their known dosages and dosage regimens. Examples of Anti-TNFα antibodies include but are not limited to: infliximab and adalimumab.

TNFα antagonists are well known to those skilled in the art and can be used in their known dosages and dosage regimens. Examples of TNFα antagonists include but are not limited to: etanercept, p38 kinase inhibitors, and TNF receptor fusion proteins.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), Mithramycin, Deoxyco-formycin, Mitomycin-C, L-Asparaginase, Interferons (especially IFN-a), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 2003 edition (Thompson PDR at Montvale, N.J. 07645-1742, USA); the disclosure of which is incorporated herein by reference thereto.

As used herein, a microtubule affecting agent is a compound that interferes with cellular mitosis, i.e., having an anti-mitotic effect, by affecting microtubule formation and/or action. Such agents can be, for instance, microtubule stabilizing agents or agents that disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) *Science,* 274:2009) estramustine, nocodazole, MAP4, and the like. Examples of such agents are also described in the scientific and patent literature, see, e.g., Bulinski (1997) *J. Cell Sci.* 110:3055-3064; Panda (1997) *Proc. Natl. Acad. Sci. USA* 94:10560-10564; Muhlradt (1997) *Cancer Res.* 57:3344-3346; Nicolaou (1997) *Nature* 387:268-272; Vasquez (1997) *Mol. Biol. Cell.* 8:973-985; Panda (1996) *J. Biol. Chem.* 271:29807-29812.

Particularly preferred agents are compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) *Oncology,* 6: 17-23, Horwitz (1992) *Trends Pharmacol. Sci.* 13: 134-146, Rowinsky (1990) *J. Natl. Canc. Inst.* 82: 1247-1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) *Cancer Chemother. Pharmacol.* 41:3747).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

Compounds with possible tubulin polymerization activity can be screened in vitro. In a preferred embodiment, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) *Lab. Anim. Sci.,* 45(2):145-150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) *J. Molec. Biol.,* 89: 737-758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition, their administration is described in the standard literature.

The amount and frequency of administration of the compounds of formula 1.0, or a pharmaceutically acceptable salt thereof, and the chemotherapeutic agents and/or radiation therapy will be regulated according to the judgment of the attending clinician (physician) considering such factors as age, condition and size of the patient as well as severity of the disease being treated. A dosage regimen of the compound of formula 1.0, or a pharmaceutically acceptable salt thereof, can be oral administration of from 10 mg to 2000 mg/day, preferably 10 to 1000 mg/day, more preferably 50 to 600 mg/day, in two to four (preferably two) divided doses, to block tumor growth. Intermittant therapy (e.g., one week out of three weeks or three out of four weeks) may also be used.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

In the methods of this invention, a compound of formula 1.0, or pharmaceutically acceptable salts thereof, is administered concurrently or sequentially with a chemotherapeutic agent and/or radiation. Thus, it is not necessary that, for example, the chemotherapeutic agent and the compound of formula 1.0, or pharmaceutically acceptable salts thereof, or the radiation and the compound of formula 1.0, or a pharmaceutically acceptable salt thereof, should be administered simultaneously or essentially simultaneously. The advantage of a simultaneous or essentially simultaneous administration is well within the determination of the skilled clinician.

Also, in general, the compound of formula 1.0, or a pharmaceutically acceptable salt thereof, and the chemotherapeutic agent do not have to be administered in the same pharmaceutical composition, and may, because of different physical and chemical characteristics, have to be administered by different routes. For example, the compound of formula 1.0, or a pharmaceutically acceptable salt thereof, may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of a compound of formula 1.0, or a pharmaceutically acceptable salt thereof, and chemotherapeutic agent and/or radiation will depend upon the diagnosis of the attending physicians and their judgement of the condition of the patient and the appropriate treatment protocol.

The compound of formula 1.0, or a pharmaceutically acceptable salt thereof, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with the compound of formula 1.0, or a pharmaceutically acceptable salt thereof.

If the compound of formula 1.0, or a pharmaceutically acceptable salt thereof, and the chemotherapeutic agent and/or radiation are not administered simultaneously or essentially simultaneously, then the initial order of administration of the compound of formula 1.0, or a pharmaceutically acceptable salt thereof, and the chemotherapeutic agent and/or radiation, may not be important. Thus, the compound of formula 1.0, or a pharmaceutically acceptable salt thereof, may be administered first, followed by the administration of the chemotherapeutic agent and/or radiation; or the chemotherapeutic agent and/or radiation may be administered first, followed by the administration of the compound of formula 1.0, or a pharmaceutically acceptable salt thereof. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

For example, the chemotherapeutic agent and/or radiation may be administered first, especially if it is a cytotoxic agent, and then the treatment continued with the administration of the compound of formula 1.0, or a pharmaceutically acceptable salt thereof, followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent—i.e., the compound of formula 1.0, or a pharmaceutically acceptable salt thereof, chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radio-logical studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Certain compounds of the invention may exist in different stereoisomeric forms (e.g., enantiomers, diastereoisomers and atropisomers). The invention contemplates all such stereoisomers both in pure form and in admixture, including racemic mixtures. Isomers can be prepared using conventional methods.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC 1974 Recommendations*. The use of the terms "salt", "solvate" "prodrug" and the like, is intended to equally apply to the salt, solvate and prodrug of enantiomers, stereoisomers, rotamers, tautomers, racemates or prod rugs of the inventive compounds.

This invention also includes prodrugs of the compounds of this invention. The term "prodrug," as used herein, represents compounds that are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

This invention also includes the compounds of this invention in isolated and purified form.

Polymorphic forms of the compounds of formula 1.0, and of the salts, solvates and prodrugs of the compounds of formula 1.0, are intended to be included in the present invention.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

The compounds of formula 1.0 form salts that are also within the scope of this invention. Reference to a compound of formula 1.0 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula 1.0 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the formula 1.0 may be formed, for example, by reacting a compound of formula 1.0 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, Journal of Pharmaceutical Sciences (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of formula 1.0, and salts, solvates and prodrugs thereof, may exist in their tautomeric form (for example, as an amide or imino ether). All such tautomeric forms are contemplated herein as part of the present invention.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, $18^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal composition can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

BIOLOGICAL EXAMPLES

The compounds of the present invention are useful in the treatment of CXC-chemokine mediated conditions and diseases. This utility would be manifested in their ability to inhibit IL-8 and GRO-α chemokine which could be demonstrated by the following in vitro assays.

Receptor Binding Assays:

CXCR1 SPA Assay

For each well of a 96 well plate, a reaction mixture of 10 μg hCXCR1-CHO overexpressing membranes (Biosignal) and 200 μg/well WGA-SPA beads (Amersham) in 100 μl can be prepared in CXCR1 assay buffer (25 mM HEPES, pH 7.8, 2 mM $CaCl_2$, 1 mM $MgCl_2$, 125 mM NaCl, 0.1% BSA) (Sigma). A 0.4 nM stock of ligand, [125I]-IL-8 (NEN) can be prepared in the CXCR1 assay buffer. 20× stock solutions of test compounds can be prepared in DMSO (Sigma). A 6× stock solution of IL-8 (R&D) can be prepared in CXCR2 assay buffer. The above solutions can be added to a 96-well assay plate (PerkinElmer) as follows: 10 μl test compound or DMSO, 40 μl CXCR1 assay buffer or IL-8 stock, 100 μl of reaction mixture, 50 μl of ligand stock (Final [Ligand]=0.1 nM). The assay plates can be shaken for 5 minutes on plate shaker, then incubated for 8 hours before cpm/well can be determined in Microbeta Trilux counter (PerkinElmer). % Inhibition of Total binding-NSB (250 nM IL-8) can be determined for IC50 values.

CXCR2 SPA Assay

For each well of a 96 well plate, a reaction mixture of 4 μg hCXCR2-CHO overexpressing membranes (Biosignal) and 200 μg/well WGA-SPA beads (Amersham) in 100 μl can be prepared in CXCR2 assay buffer (25 mM HEPES, pH 7.4, 2 mM $CaCl_2$, 1 mM $MgCl_2$). A 0.4 nM stock of ligand, [125I]-IL-8 (NEN), can be prepared in the CXCR2 assay buffer. 20× stock solutions of test compounds can be prepared in DMSO (Sigma). A 6× stock solution of GRO-α (R&D) can be prepared in CXCR2 assay buffer. The above solutions can be added to a 96-well assay plate (PerkinElmer or Corning) as follows: 10 μl test compound or DMSO, 40 ul CXCR2 assay buffer or GRO-α stock, 100 μl of reaction mixture, 50 μl of ligand stock (Final [Ligand]=0.1 nM). When 40× stock solutions of test compounds in DMSO can be prepared, then the above protocol can be used except instead 5 μl test compound or DMSO and 45 μl CXCR2 assay buffer can be used. The assay plates can be shaken for 5 minutes on a plate shaker, then incubated for 2-8 hours before cpm/well can be determined in Microbeta Trilux counter (PerkinElmer). % Inhibition of total binding minus non-specific binding (250 nM Gro-α or 50 μM antagonist) can be determined and IC50 values can be calculated.

Calcium Fluorescence Assay (FLIPR)

HEK 293 cells stably transfected with hCXCR2 and Gαι/q can be plated at 10,000 cells per well in a Poly-D-Lysine Black/Clear plate (Becton Dickinson) and can be incubated 48 hours at 5% $CO_2$, 37° C. The cultures can then be incubated with 4 mM fluo-4, AM (Molecular Probes) in Dye Loading Buffer (1% FBS, HBSS w. Ca & Mg, 20 mM HEPES (Cellgro), 2.5 mM Probenicid (Sigma) for 1 hour. The cultures can be washed with wash buffer (HBSS w Ca, & Mg, 20 mM HEPES, Probenicid (2.5 mM)) three times, then 100 μl/well wash buffer can be added.

During incubation, compounds can be prepared as 4× stocks in 0.4% DMSO (Sigma) and wash buffer and can be added to their respective wells in the first addition plate. IL-8 or GRO-α (R&D Systems) concentrations can be prepared 4× in wash buffer+0.1% BSA and can be added to their respective wells in second addition plate.

Culture plate and both addition plates can then be placed in the FLIPR imaging system to determine change in calcium fluorescence upon addition of compound and then ligand. Briefly, 50 μl of compound solutions or DMSO solution can be added to respective wells and change in calcium fluorescence can be measured by the FLIPR for 1 minute. After a 3 minute incubation within the instrument, 50 μl of ligand can then be added and the change in calcium fluorescence can be measured by the FLIPR instrument for 1 minute. The area under each stimulation curve can be determined and values can be used to determine % Stimulation by compound (agonist) and % Inhibition of Total Calcium response to ligand (0.3 nM IL-8 or GRO-α) for IC50 values of the test compounds.

Chemotaxis Assays for 293-CXCR2

A chemotaxis assay can be setup using Fluorblok inserts (Falcon) for 293-CXCR2 cells (HEK-293 cells overexpressing human CXCR2). The standard protocol used at present is as follows:
1. Inserts can be coated with collagenIV (2 ug/ml) for 2 hrs at 37° C.
2. The collagen can be removed and inserts can be allowed to air dry overnight.
3. Cells can be labeled with 10 uM calcein AM (Molecular Probes) for 2 hrs. Labeling can be done in complete media with 2% FBS.
4. Dilutions of compound can be made in minimal media (0.1% BSA) and can be placed inside the insert which can be positioned inside the well of a 24 well plate. Within the well can be IL-8 at a concentration of 0.25 nM in minimal media. Cells can be washed and can be resuspended in minimal media and can be placed inside the insert at a concentration of 50,000 cells per insert.
5. Plate can be incubated for 2 hrs and inserts can be removed and can be placed in a new 24 well. Fluorescence can be detected at excitation=485 nM and emission=530 nM.

Cytotoxicity Assays

A cytotoxicity assay for CXCR2 compounds can be conducted on 293-CXCR2 cells. Concentrations of compounds can be tested for toxicity at high concentrations to determine if they may be used for further evaluation in binding and cell based assays. The protocol is as follows:
1. 293-CXCR2 cells can be plated overnight at a concentration of 5000 cells per well in complete media.
2. Dilutions of compound can be made in minimal media w/0.1% BSA. Complete media can be poured off and the dilutions of compound can be added. Plates can be incubated for 4, 24 and 48 hrs. Cells can be labeled with 10 uM calcein AM for 15 minutes to determine cell viability. Detection method can be the same as above.

Soft Agar Assay 10,000 SKMEL-5 cells/well can be placed in a mixture of 1.2% agar and complete media with various dilutions of compound. Final concentration of agar can be 0.6%. After 21 days viable cell colonies can be stained with a solution of MTT (1 mg/ml in PBS). Plates can then be scanned to determine colony number and size. $IC_{50}$ can be determined by comparing total area vs. compound concentration.

Rat Carrageenan-Induced Thermal Hyperalgesia

Male Sprague-Dawley rats (Charles River Laboratories; 150-200 gm) can be maintained under normal housing and lighting conditions, with food and water supplied ad libitum. Each animal can be tested for its baseline paw withdrawal response to a heat source by placement of the animal into a plantar testing unit (Ugo Basile, Italy), in which a light source is moved under its paw and the time of withdrawal is measured. The animals can then be dosed orally with a compound of this invention, and then can be injected intraplantarly with 2-3 mg lambda carrageenan (FMC Colloids) in 100 ul of saline while under isofurane anesthesia. Three hours later, the animals can be re-measured for their withdrawal response to the heat source. Plantar tissue can also be analyzed for myeloperoxidase levels as a surrogate for neutrophil infiltration.

Compounds of formula 1.0 may be produced by processes known to those skilled in the art, by processes similar to those described in WO 02/083624 (published Oct. 24, 2002), by processes similar to those described in U.S. 2004/0106794 (published Jun. 3, 2004), by processes similar to those described in WO 2004/011418 (published Feb. 5, 2004), and in the preparations and examples below. The disclosures of WO 02/083624, U.S. 2004/0106794, and WO 2004/011418 are incorporated herein by reference thereto.

Compounds useful in this invention are exemplified by the following examples, which examples should not be construed as limiting the scope of the disclosure.

Example 1

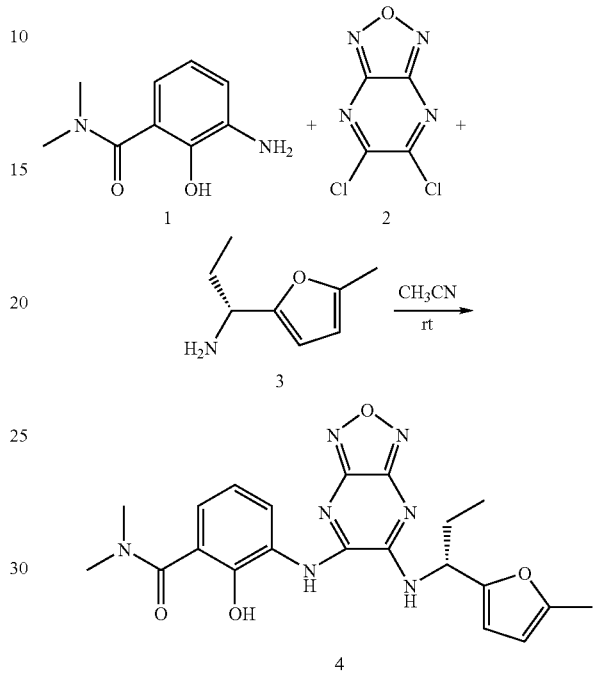

To a stirred solution of the commercially available 5,6-Dichloro-[1,2,5]oxadiazolo[3,4-b]pyrazine 2 in anhydrous acetonitrile was added the furyl amine 3 and stirred overnight at room temperature. The crude reaction mixture was then treated with the phenolic amine 1 and stirring was continued for another 12 hours. The solvent was removed and the product was purified by preparative thin layer chromatography using dichloromethane and methanol (20:1) to obtain the diamino compound 4 (Yield=9.6%, M+1=438.1). Compound 4 had a CXCR2 $K_i$ of 196 nM, and a CXCR1 $K_i$ of 4.22 µM.

Examples 2 to 52

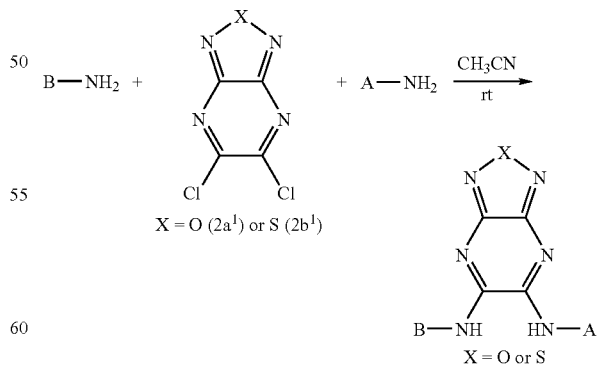

If one were to follow a procedure similar to that in Example 1, but using the amines B—$NH_2$ and A-$NH_2$, as set forth in Table 1, with either 5,6-dichloro-[1,2,5]oxadiazolo[3,4-b]pyrazine ($2a^1$) or 5,6-dichloro-[1,2,5]thiadiazolo[3,4-b]pyrazine ($2b^1$), the final compounds in Table 1 could be prepared.

TABLE 1

| B-NH₂ | A-NH₂ | Final Compound |
|---|---|---|
| (structure) | (structure) | Ex. No. 2a: X = O  Ex No. 2b: X = S |
| (structure) | (structure) | Ex. No. 3a: X = O  Ex No. 3b: X = S |
| (structure) | (structure) | Ex. No. 4a: X = O  Ex No. 4b: X = S |
| (structure) | (structure) | Ex. No. 5a: X = O  Ex No. 5b: X = S |
| (structure) | (structure) | Ex. No. 6a: X = O  Ex No. 6b: X = S |

TABLE 1-continued

| B-NH₂ | A-NH₂ | Final Compound |
|---|---|---|
| | | Ex. No. 7a: X = O  Ex No. 7b: X = S |
| | | Ex. No. 8a: X = O  Ex No. 8b: X = S |
| | | Ex. No. 9a: X = O  Ex No. 9b: X = S |
| | | Ex. No. 10a: X = O  Ex No. 10b: X = S |
| | | Ex. No. 11a: X = O  Ex No. 11b: X = S |

TABLE 1-continued

| B-NH₂ | A-NH₂ | Final Compound |
|---|---|---|
| | | Ex. No. 12a: X = O   Ex No. 12b: X = S |
| | | Ex. No. 13a: X = O   Ex No. 13b: X = S |
| | | Ex. No. 14a: X = O   Ex No. 14b: X = S |
| | | Ex. No. 15a: X = O   Ex No. 15b: X = S |
| | | Ex. No. 16a: X = O   Ex No. 16b: X = S |

TABLE 1-continued

| B-NH₂ | A-NH₂ | Final Compound |
|---|---|---|
| | | Ex. No. 17a: X = O  Ex No. 17b: X = S |
| | | Ex. No. 18a: X = O  Ex No. 18b: X = S |
| | | Ex. No. 19a: X = O  Ex No. 19b: X = S |
| | | Ex. No. 20a: X = O  Ex No. 20b: X = S |
| | | Ex. No. 21a: X = O  Ex No. 21b: X = S |

TABLE 1-continued
| B-NH₂ | A-NH₂ | Final Compound |
|---|---|---|
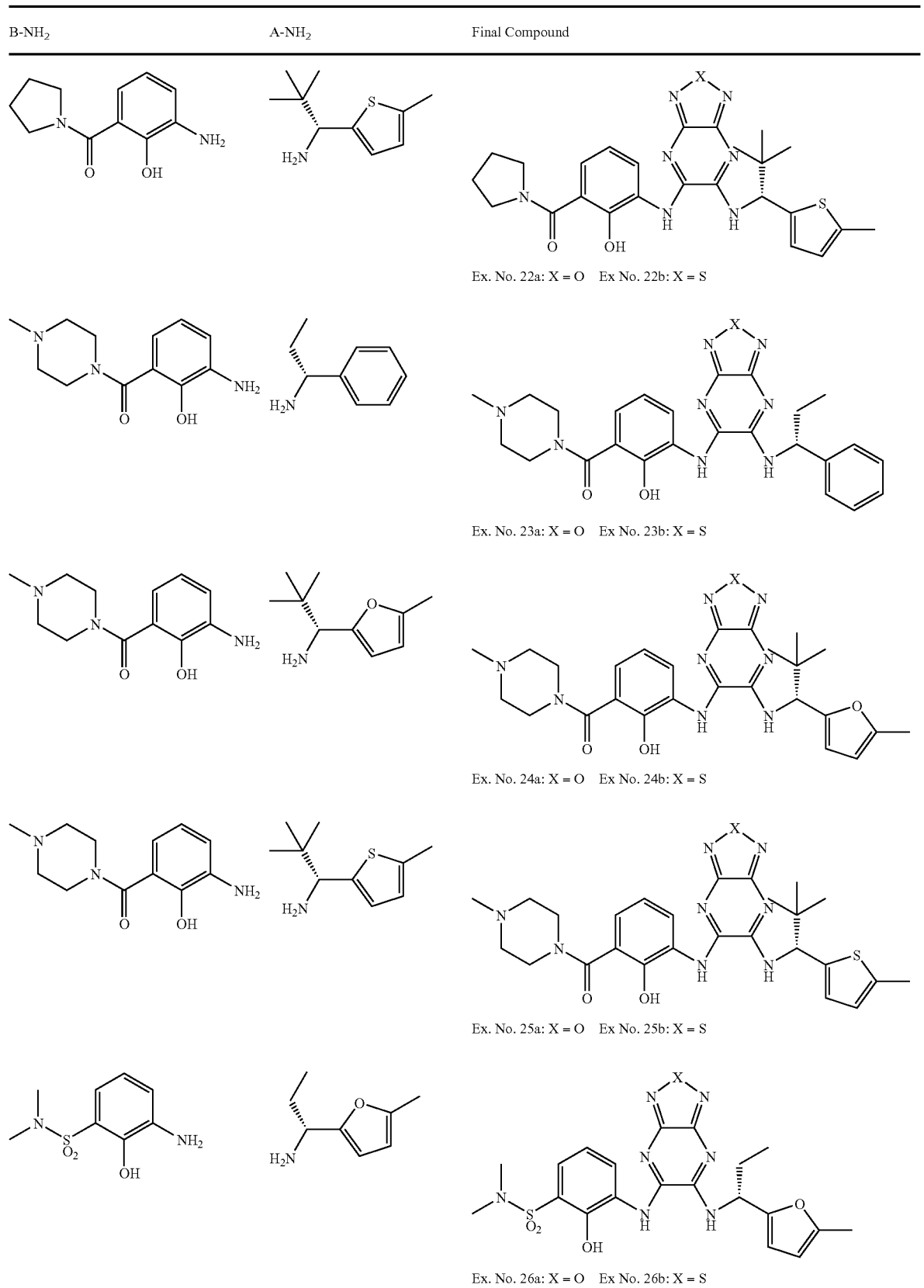
Ex. No. 22a: X = O   Ex No. 22b: X = S
Ex. No. 23a: X = O   Ex No. 23b: X = S
Ex. No. 24a: X = O   Ex No. 24b: X = S
Ex. No. 25a: X = O   Ex No. 25b: X = S
Ex. No. 26a: X = O   Ex No. 26b: X = S TABLE 1-continued
| B-NH$_2$ | A-NH$_2$ | Final Compound |
|---|---|---|
| 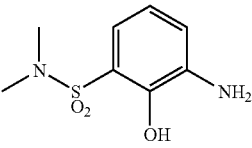 | 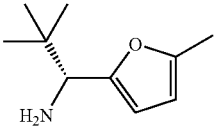 | 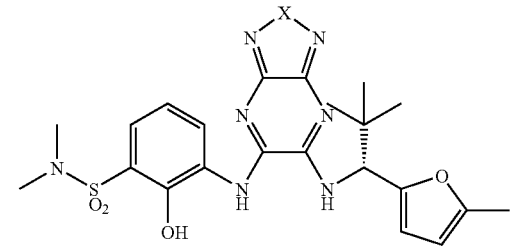<br>Ex. No. 27a: X = O   Ex No. 27b: X = S |
| 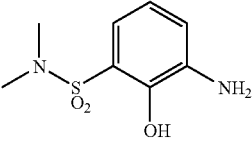 | 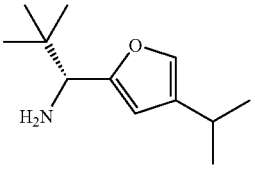 | 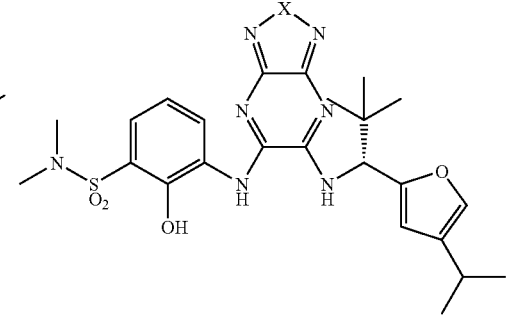<br>Ex. No. 28a: X = O   Ex No. 28b: X = S |
| 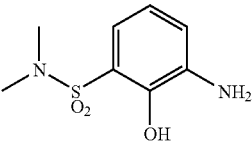 | 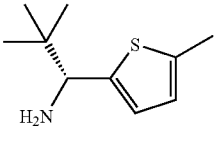 | 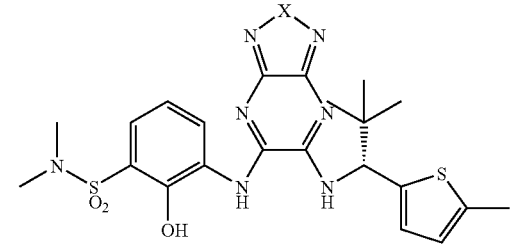<br>Ex. No. 29a: X = O   Ex No. 29b: X = S |
| 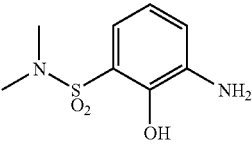 | 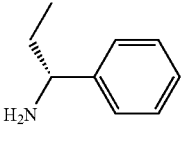 | 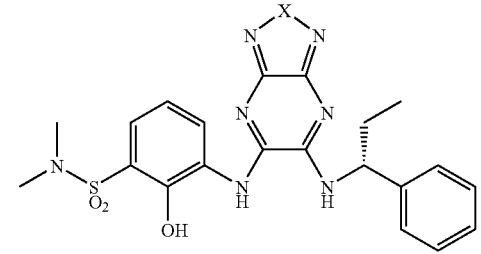<br>Ex. No. 30a: X = O   Ex No. 30b: X = S |
| 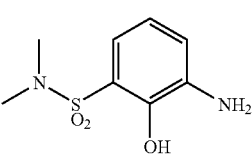 | 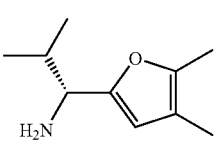 | 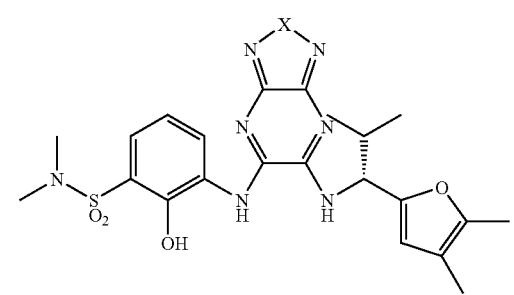<br>Ex. No. 31a: X = O   Ex No. 31b: X = S |

TABLE 1-continued

| B-NH₂ | A-NH₂ | Final Compound |
|---|---|---|
| (3-amino-2-hydroxyphenyl)-N,N-dimethylsulfonamide | (S)-1-(5-methylfuran-2-yl)-2,2,2-trifluoroethan-1-amine | Ex. No. 32a: X = O  Ex No. 32b: X = S |
| (3-amino-2-hydroxyphenyl)pyrrolidin-1-ylsulfonamide | (S)-1-(5-methylfuran-2-yl)propan-1-amine | Ex. No. 33a: X = O  Ex No. 33b: X = S |
| (3-amino-2-hydroxyphenyl)pyrrolidin-1-ylsulfonamide | (S)-2,2-dimethyl-1-(5-methylfuran-2-yl)propan-1-amine | Ex. No. 34a: X = O  Ex No. 34b: X = S |
| (3-amino-2-hydroxyphenyl)pyrrolidin-1-ylsulfonamide | (S)-2,2-dimethyl-1-(4-isopropylfuran-2-yl)propan-1-amine | Ex. No. 35a: X = O  Ex No. 35b: X = S |
| (3-amino-2-hydroxyphenyl)pyrrolidin-1-ylsulfonamide | (S)-2,2-dimethyl-1-(5-methylthiophen-2-yl)propan-1-amine | Ex. No. 36a: X = O  Ex No. 36b: X = S |

TABLE 1-continued
| B-NH₂ | A-NH₂ | Final Compound |
|---|---|---|
| 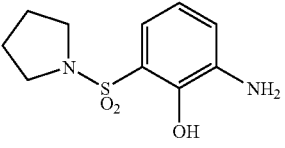 | 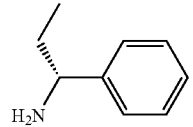 | 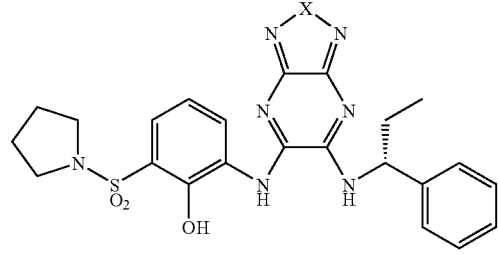<br>Ex. No. 37a: X = O   Ex No. 37b: X = S |
| 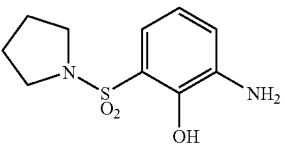 | 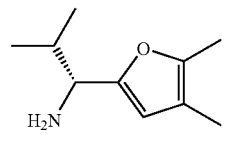 | 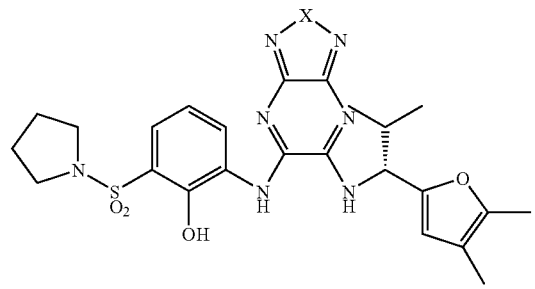<br>Ex. No. 38a: X = O   Ex No. 38b: X = S |
| 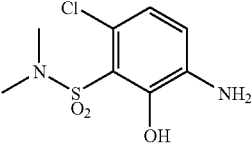 | 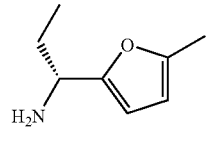 | 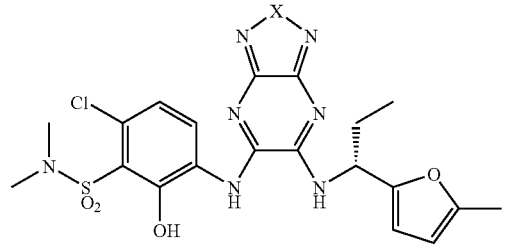<br>Ex. No. 39a: X = O   Ex No. 39b: X = S |
| 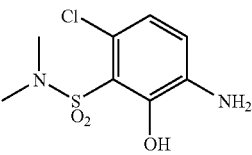 | 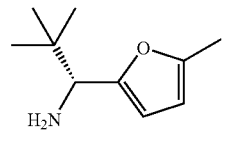 | 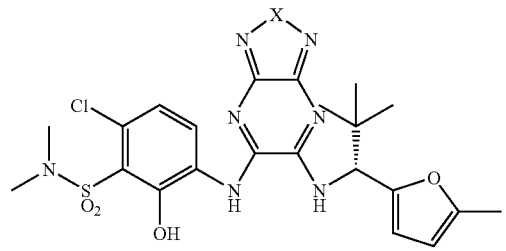<br>Ex. No. 40a: X = O   Ex No. 40b: X = S |
| 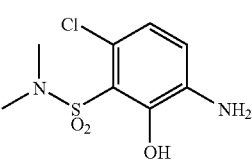 | 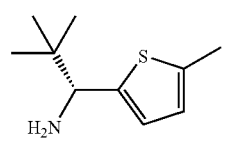 | 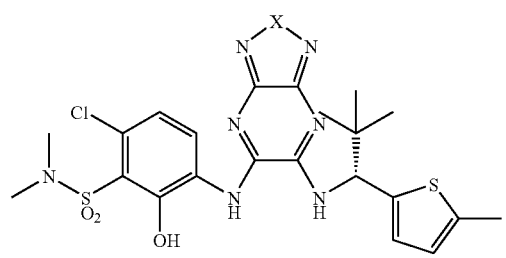<br>Ex. No. 41a: X = O   Ex No. 41b: X = S |

TABLE 1-continued

| B-NH₂ | A-NH₂ | Final Compound |
|---|---|---|
| (structure) | (structure) | Ex. No. 42a: X = O  Ex No. 42b: X = S |
| (structure) | (structure) | Ex. No. 43a: X = O  Ex No. 43b: X = S |
| (structure) | (structure) | Ex. No. 44a: X = O  Ex No. 44b: X = S |
| (structure) | (structure) | Ex. No. 45a: X = O  Ex No. 45b: X = S |
| (structure) | (structure) | Ex. No. 46a: X = O  Ex No. 46b: X = S |

TABLE 1-continued

| B-NH₂ | A-NH₂ | Final Compound |
|---|---|---|
| (structure) | (structure) | Ex. No. 47a: X = O  Ex No. 47b: X = S |
| (structure) | (structure) | Ex. No. 48a: X = O  Ex No. 48b: X = S |
| (structure) | (structure) | Ex. No. 49a: X = O  Ex No. 49b: X = S |
| (structure) | (structure) | Ex. No. 50a: X = O  Ex No. 50b: X = S |
| (structure) | (structure) | Ex. No. 51a: X = O  Ex No. 51b: X = S |

TABLE 1-continued

| B-NH₂ | A-NH₂ | Final Compound |
|---|---|---|
| 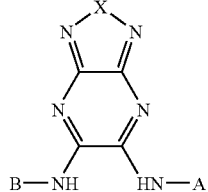 | 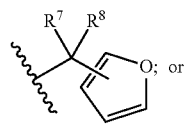 | 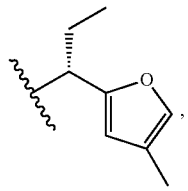<br>Ex. No. 52a: X = O   Ex No. 52b: X = S |

While the present invention has been described in conjunction with specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

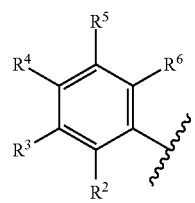

(1.0)

and the pharmaceutically acceptable salts thereof, wherein:

X is O;

A is:

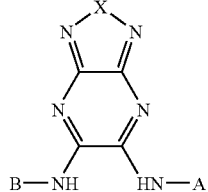

A8

A is A8 wherein said A group is substituted with 1 to 6 independently selected alkyl groups;

B is:

(B1 structure with R², R³, R⁴, R⁵, R⁶ on phenyl ring)

B1

$R^2$ is OH;
$R^3$ is —C(O)NR$^{13}$R$^{14}$ wherein R$^{13}$ and R$^{14}$ are the same or different alkyl group;
$R^4$, $R^5$, and $R^6$ are H; and
$R^7$ is H and $R^8$ is alkyl.

2. The compound of claim 1 wherein $R^{13}$ and $R^{14}$ are methyl.

3. The compound of claim 1 wherein A is A8 wherein the furan ring is substituted.

4. The compound of claim 1 wherein A is selected from the group consisting of:

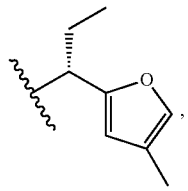 A8.4

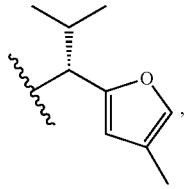 A8.5

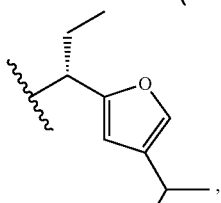 A8.7

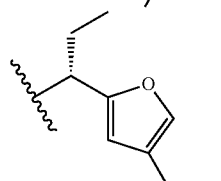 A8.8

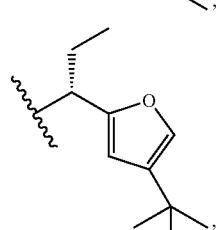 A8.9

-continued
A8.12 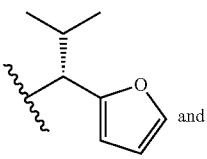
A8.14
A8.15
A8.18
A8.19
A8.20
A8.21
A8.23
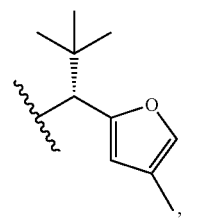
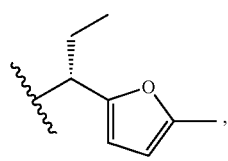
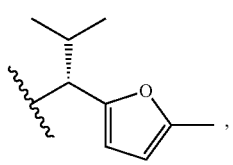
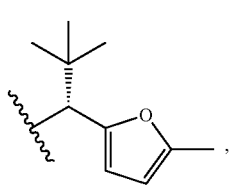
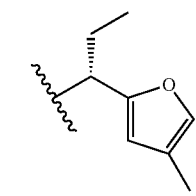
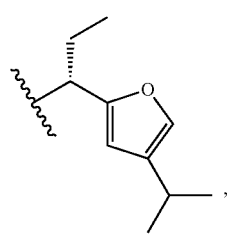
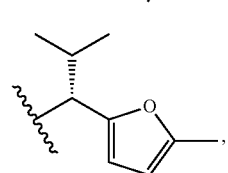
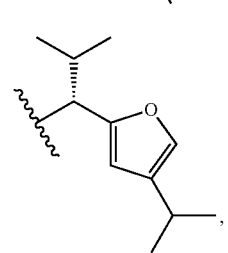
A8.24 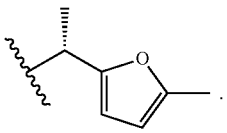 and
A8.25
5. The compound of claim 1 wherein said compound is a calcium salt.
6. The compound of claim 1 wherein said compound is a sodium salt.
7. The compound of claim 1 selected from the group consisting of
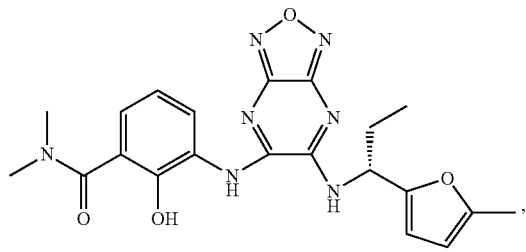
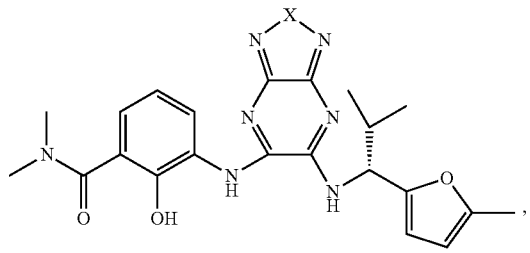
Ex No. 2a: X = O
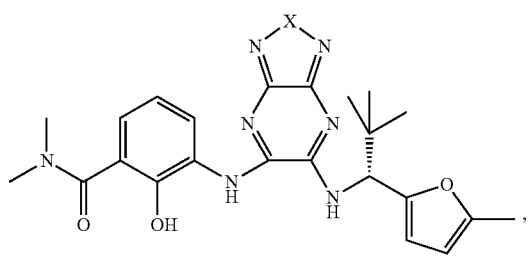
Ex No. 3a: X = O

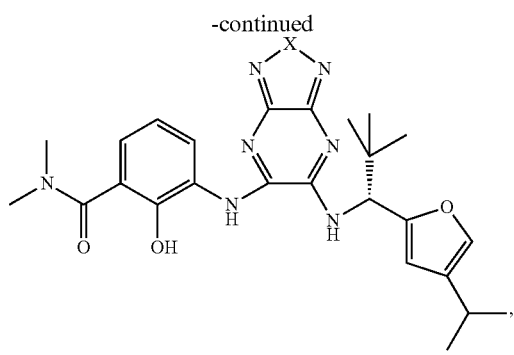
Ex No. 4a: X = O
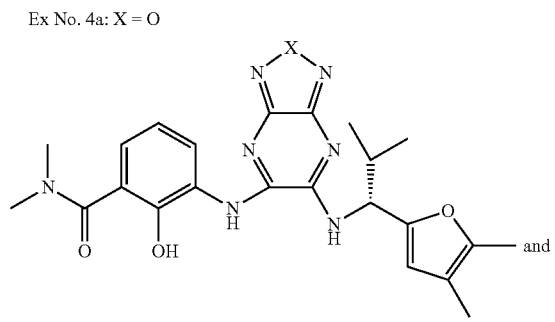
Ex No. 8a: X=O
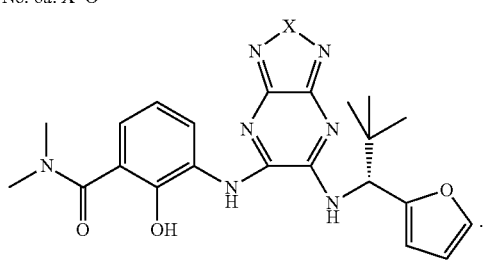
Ex No. 10a: X=O
8. The compound of claim 1 selected from the group consisting of
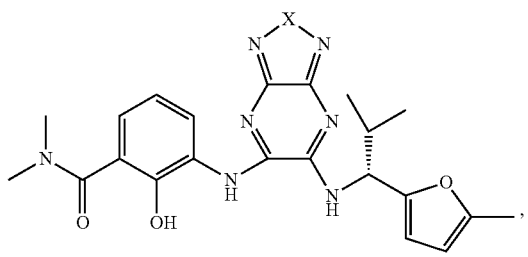
Ex No. 2a: X = O
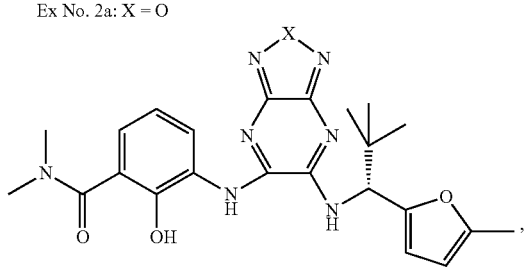
Ex No. 3a: X = O
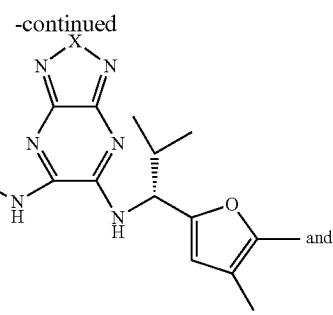
Ex No. 8a: X = O
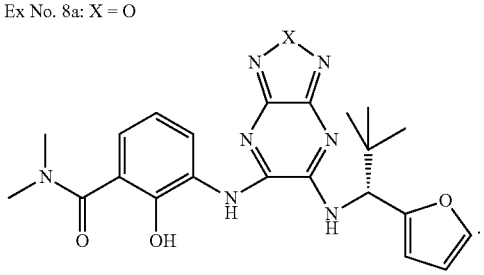
Ex No. 10a: X = O
9. The compound of claim 1 selected from the group consisting of
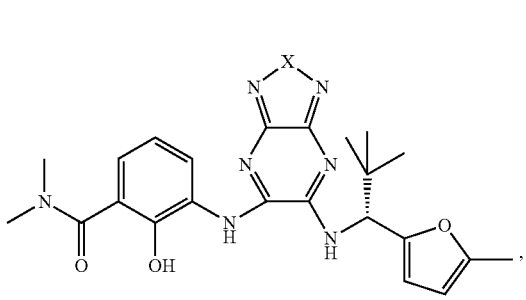
Ex No. 3a: X = O
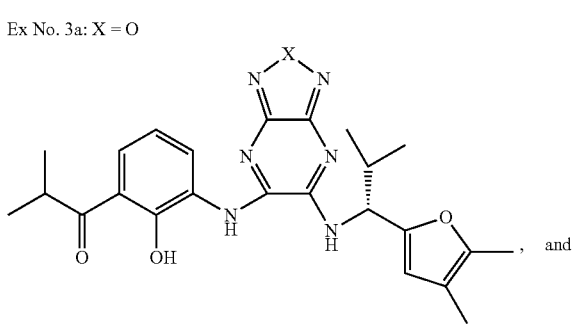
Ex No. 8a: X = O
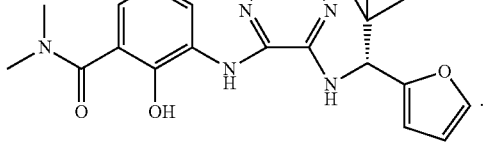
Ex No. 10a: X = O 10. The compound of claim 7 wherein said compound is a calcium or sodium salt.

11. A pharmaceutical composition comprising an effective amount of at least one compound of claim 1, or a pharmaceutically acceptable salt thereof, in combination with a pharmaceutically acceptable carrier.

12. A pharmaceutical composition comprising an effective amount of at least one compound of claim 7, or a pharmaceutically acceptable salt thereof, in combination with a pharmaceutically acceptable carrier.

* * * * *